US012343566B2

(12) United States Patent
Letourneau et al.

(10) Patent No.: US 12,343,566 B2
(45) Date of Patent: Jul. 1, 2025

(54) QUALITY ASSURANCE FOR MR-LINAC

(71) Applicant: Elekta LTD., Montreal (CA)

(72) Inventors: Daniel Letourneau, Toronto (CA); Elaine Conneely, Hamilton (CA)

(73) Assignee: Elekta LTD., Montreal (CA)

( * ) Notice: Subject to any disclaimer, the term of this patent is extended or adjusted under 35 U.S.C. 154(b) by 0 days.

(21) Appl. No.: 18/636,853

(22) Filed: Apr. 16, 2024

(65) Prior Publication Data
US 2024/0285975 A1    Aug. 29, 2024

Related U.S. Application Data

(63) Continuation of application No. 17/309,009, filed as application No. PCT/CA2019/000144 on Oct. 11, 2019, now Pat. No. 12,070,623.

(60) Provisional application No. 62/744,875, filed on Oct. 12, 2018.

(51) Int. Cl.
- *A61N 5/00* (2006.01)
- *A61N 5/10* (2006.01)
- *G16H 30/40* (2018.01)

(52) U.S. Cl.
CPC ......... *A61N 5/1075* (2013.01); *A61N 5/1045* (2013.01); *G16H 30/40* (2018.01); *A61N 2005/1055* (2013.01); *A61N 2005/1076* (2013.01)

(58) Field of Classification Search
CPC .......... A61N 2005/1055; A61N 5/1045; A61N 5/1075
See application file for complete search history.

(56) References Cited

U.S. PATENT DOCUMENTS

| 7,476,867 B2 | 1/2009 | Fritsch et al. |
| 8,119,978 B2 | 2/2012 | Islam et al. |
| 9,211,101 B2 | 12/2015 | Wong et al. |

(Continued)

FOREIGN PATENT DOCUMENTS

| CN | 101390190 A | 3/2009 |
| CN | 104204852 A | 12/2014 |

(Continued)

OTHER PUBLICATIONS

"U.S. Appl. No. 17/309,009, Notice of Allowance mailed Jan. 24, 2024", 10 pgs.

(Continued)

*Primary Examiner* — Dani Fox
(74) *Attorney, Agent, or Firm* — Schwegman Lundberg & Woessner, P.A.

(57) ABSTRACT

The present disclosure includes procedures to automate quality assurance testing for radiotherapy equipment that includes MR-Linac devices that are agnostic as to the manufacturer and vendor of the equipment. The present disclosure includes a process for performing a validation procedure for the linear accelerator of the MR-Linac device. The present disclosure includes a process for analyzing quality of the images produced by the MR imaging device of the MR-Linac device. The present disclosure includes a process for combining performance of a validation procedure for the linear accelerator of the MR-Linac device and the analysis of the quality of the images produced by the MR imaging device of the MR-Linac device.

20 Claims, 13 Drawing Sheets

(56) References Cited

U.S. PATENT DOCUMENTS

| | | | |
|---|---|---|---|
| 9,283,405 | B2 | 3/2016 | Wong |
| 9,381,376 | B2 | 7/2016 | Toimela et al. |
| 9,844,358 | B2 | 12/2017 | Wiggers et al. |
| 9,943,705 | B2 | 4/2018 | Chappelow et al. |
| 10,022,564 | B2 | 7/2018 | Thieme et al. |
| 12,070,623 | B2 | 8/2024 | Letourneau et al. |
| 2002/0080912 | A1 | 6/2002 | Mackie et al. |
| 2002/0181660 | A1 | 12/2002 | Reinstein et al. |
| 2004/0022363 | A1 | 2/2004 | Ghelmansarai |
| 2005/0013406 | A1 | 1/2005 | Dyk et al. |
| 2011/0201919 | A1 | 8/2011 | Allen et al. |
| 2015/0036806 | A1 | 2/2015 | Wong |
| 2015/0088449 | A1 | 3/2015 | Foxall et al. |
| 2015/0094514 | A1 | 4/2015 | Gaudio |
| 2016/0114190 | A1 | 4/2016 | Brown et al. |
| 2016/0144200 | A1* | 5/2016 | Leach .................. A61N 5/1077 324/322 |
| 2016/0225132 | A1 | 8/2016 | Han et al. |
| 2016/0361567 | A1 | 12/2016 | Chappelow et al. |
| 2017/0165505 | A1 | 6/2017 | Arican et al. |
| 2017/0199971 | A1 | 7/2017 | Yaddanapudi et al. |
| 2017/0252579 | A1* | 9/2017 | Kilby .................. A61N 5/1071 |
| 2018/0085168 | A1 | 3/2018 | Valdes et al. |
| 2018/0136295 | A1* | 5/2018 | Tadic .................... G01R 33/58 |
| 2018/0211725 | A1 | 7/2018 | Purdie et al. |
| 2022/0001210 | A1 | 1/2022 | Letourneau et al. |

FOREIGN PATENT DOCUMENTS

| | | | |
|---|---|---|---|
| CN | 113196414 | A | 7/2021 |
| CN | 113196414 | | 4/2025 |
| EP | 2359905 | A1 | 8/2011 |
| EP | 2774537 | A1 * | 9/2014 ........... A61B 5/0035 |
| EP | 2865419 | A1 | 4/2015 |
| EP | 3135338 | A1 | 3/2017 |
| EP | 3864665 | | 4/2025 |
| JP | 2017127637 | A | 7/2017 |
| KR | 20100111985 | A | 10/2010 |
| KR | 20130059668 | A | 6/2013 |
| KR | 20170096497 | A | 8/2017 |
| WO | 2015060691 | | 4/2015 |
| WO | WO-2015196109 | A2 | 12/2015 |
| WO | WO-2016191883 | A1 | 12/2016 |
| WO | WO-2018081420 | A1 | 5/2018 |
| WO | WO-2018177910 | A1 | 10/2018 |
| WO | WO-2020073113 | A1 | 4/2020 |

OTHER PUBLICATIONS

"U.S. Appl. No. 17/309,009, Response filed Dec. 14, 2023 to Restriction Requirement mailed Nov. 17, 2023", 3 pgs.

"U.S. Appl. No. 17/309,009, Restriction Requirement mailed Nov. 17, 2023", 6 pgs.

"Australian Application Serial No. 2019356529, First Examination Report mailed May 19, 2022", 7 pgs.

"Australian Application Serial No. 2019356529, Response filed Mar. 20, 2023 to First Examination Report mailed May 19, 2022", 28 pgs.

"Australian Application Serial No. 2019356529, Subsequent Examiners Report mailed Apr. 21, 2023", 3 pgs.

"Chinese Application Serial No. 201980077937.X, Office Action mailed Mar. 1, 2024", w/ English Translation, 16 pgs.

"European Application Serial No. 19870368.8, Extended European Search Report mailed Sep. 1, 2022", 13 pgs.

"European Application Serial No. 19870368.8, Partial Supplementary European Search Report mailed May 31, 2022", 14 pgs.

"European Application Serial No. 19870368.8, Response filed Mar. 15, 2023 to Extended European Search Report mailed Sep. 1, 2022", 24 pgs.

"European Application Serial No. 19870368.8, Response to Communication persuant to Rules 161 and 162 filed Nov. 23, 2021", 17 pgs.

"International Application Serial No. PCT/CA2019/000144, International Preliminary Report on Patentability mailed Apr. 22, 2021", 9 pgs.

"International Application Serial No. PCT/CA2019/000144, International Search Report mailed Jan. 8, 2020", 4 pgs.

"International Application Serial No. PCT/CA2019/000144, Invitation to Pay Additional Fees mailed Nov. 27, 2019", 2 pgs.

"International Application Serial No. PCT/CA2019/000144, Written Opinion mailed Jan. 8, 2020", 7 pgs.

"Japanese Application Serial No. 2021-520132, Examiners Decision of Final Refusal mailed Apr. 4, 2023", w/ English translation, 13 pgs.

"Japanese Application Serial No. 2021-520132, Final Notification of Reasons for Refusal mailed Dec. 13, 2022", w/ English Translation, 22 pgs.

"Japanese Application Serial No. 2021-520132, Notification of Reasons for Refusal mailed Aug. 2, 2022", w/ English translation, 16 pgs.

"Japanese Application Serial No. 2021-520132, Response filed Mar. 10, 2026 to Final Notification of Reasons for Refusal mailed Dec. 13, 2022", w/ English Claims, 26 pgs.

"Japanese Application Serial No. 2021-520132, Response filed Nov. 21, 2022 to Notification of Reasons for Refusal mailed Aug. 2, 2022", w/ English Claims, 21 pgs.

Qiao, Ma, et al., "The Validation for Medical Accelerator and Radiotherapy Quality Assurance System", Chinese Journal of Radiological Health, No. 1, (Feb. 15, 2017), 22-24.

Sun, Baozhou, et al., "Daily QA of linear accelerators using only EPID and OBI", Medical Physics, AIP, Melville, NY, US, vol. 42, No. 10, (Sep. 8, 2015), 5584-5594.

Taylor, Harry, et al., "Risk assessment of a new acceptance testing procedure for conventional linear accelerators", Medical Physics., vol. 44, No. 11, (Sep. 30, 2017), 5610-5616.

"U.S. Appl. No. 17/309,009, Supplemental Notice of Allowability mailed Apr. 18, 2024", 2 pgs.

"U.S. Appl. No. 17/309,009, PTO Response to Rule 312 Communication mailed May 3, 2024", 1 page.

"Chinese Application Serial No. 201980077937.X, Response filed Jun. 19, 2024 to Office Action mailed Mar. 1, 2024", w current English claims, 16 pgs.

"Chinese Application Serial No. 201980077937.X, Office Action mailed Aug. 23, 2024", w English translation, 14 pgs.

"Chinese Application Serial No. 201980077937.X, Response filed Dec. 20, 2024 to Office Action mailed Aug. 23, 2024", W English Claims, 16 pgs.

"Chinese Application Serial No. 201980077937.X, Response to Telephone Examiner Interview filed Feb. 14, 2025", w English claims, 13 pgs.

Baozhou, Sun, "Daily QA of liner accelerators using only EPID and OBI", Medical Physics, AIP, Melville, NY, US, vol. 42, No. 10, (Sep. 8, 2015), 12 pgs.

\* cited by examiner

QUALITY ASSURANCE FOR MR-LINAC

CLAIM FOR PRIORITY

This application is a continuation of U.S. application Ser. No. 17/309,009, filed Apr. 12, 2021, which claims the benefit of priority to U.S. Provisional Application No. 62/744,875, filed Oct. 12, 2018, each of which is herein incorporated by reference in its entirety.

TECHNICAL FIELD

Embodiments of the present disclosure pertain generally to quality assurance techniques in radiotherapy equipment. In particular, the present disclosure pertains to performing automated quality assurance for an integrated linear accelerator and MRI imaging device (MR-Linac or MRI-Linac).

BACKGROUND

In radiosurgery or radiotherapy (collectively referred to as radiation treatment) very intense and precisely collimated doses of radiation are delivered to a target region in the body of a patient in order to treat or destroy lesions. Typically, the target region consists of a volume of tumorous tissue. Radiation treatment requires an extremely accurate spatial localization of the targeted lesions. Computed tomography ("CT"), magnetic resonance imaging ("MRI") scans, and other imaging modalities enable practitioners to precisely locate a lesion relative to skeletal landmarks or implanted fiducial markers and to control the position of the radiation source so that its beam can be precisely directed to the target tissue while avoiding adjacent critical body structures. Thus, radiation treatment necessitates high precision diagnosis and high precision radiation source control. The consequences of deviating outside the prescribed tolerances for the diagnosis and the radiation source control can be potentially devastating to a patient.

Given the need for accurate delivery of radiation therapy, regulations require quality assurance tests to be performed to ensure the radiotherapy equipment is properly operating. Such quality assurance tests are routinely performed on the radiotherapy equipment and manually analyzed by an operator to ensure proper alignment and configuration of the system prior to delivering a prescribed radiation dose to a patient. However, the manual analysis of the quality assurance tests is extremely time consuming which results in a large amount of downtime of the equipment in which patients cannot be treated. Also, the manual analysis of the tests tends to be inconsistent from one operator to another. In addition, while certain automated quality assurance processes exist for analyzing radiotherapy equipment, such techniques are typically machine specific and require use of vendor specific hardware. This also results in inconsistent determinations of quality assurance across different radiotherapy equipment manufacturers.

Overview

The present disclosure includes procedures to automate quality assurance testing for radiotherapy equipment that includes MR-Linac devices that are agnostic as to the manufacturer and vendor of the equipment. The present disclosure includes a process for performing a validation procedure for the linear accelerator of the MR-Linac device. The present disclosure includes a process for analyzing quality of the images produced by the MR imaging device of the MR-Linac device. The present disclosure includes a process for combining performance of a validation procedure for the linear accelerator of the MR-Linac device and the analysis of the quality of the images produced by the MR imaging device of the MR-Linac device.

In some embodiments, systems, methods, and computer-readable media are provided for validating an operation of a radiotherapy apparatus comprising an integrated linear accelerator and MRI imaging device (MR-Linac). The systems, methods, and computer-readable media perform operations including: selecting a validation procedure associated with the linear accelerator of the MR-Linac; retrieving, based on the selected validation procedure, configuration information for a multi-leaf collimator (MLC) of the MR-Linac; obtaining a plurality of images from an imaging detector each associated with given radiation beam of a plurality of radiation beams that passes through the MLC that has been adjusted based on the configuration information; processing the plurality of images to determine a characteristic of the MR-Linac; and determining whether the MR-Linac is operating within a valid range based on processing of the plurality of images.

In some implementations, the systems, methods, and computer-readable media perform operations including comparing the determined characteristic with an allowable threshold associated with the selected validation procedure and adjusting one or more characteristics of the MR-Linac in response to determining that the MR-Linac is operating outside of the valid range.

In some implementations, the one or more characteristics are determined based on the selected validation procedure.

In some implementations, the systems, methods, and computer-readable media perform operations including automatically adjusting the MLC in response to retrieving the configuration information and selection of the validation procedure.

In some implementations, the plurality of validation procedures comprises a leaf position validation procedure of the MLC, a radiation source and imaging detector movement validation procedure, a linear accelerator and MRI imaging device alignment validation procedure, and a linear accelerator flatness symmetry validation procedure.

In some implementations, the selected validation procedure comprises a leaf position validation procedure, wherein the plurality of images include at least seven images obtained at a same gantry angle of the MR-Linac, wherein the characteristic comprises leaf and jaw positions relative to nominal leaf and jaw positions, and wherein the allowable threshold comprises one millimetre.

In some implementations, first, second and third of the seven images are processed to determine a radiation isocenter, the configuration information indicates a first position for a first and second sets of leaves of the MLC, a second position for a third set of leaves of the MLC between the first and second sets of leaves, and the operations further include: segmenting the first, second and third images; computing a center of mass for each of the segmented first, second and third images; fitting a circular function to the computed center of masses; determining a radiation isocenter associated with each of the first, second and third images based on a center of the circular function; and detecting motion in the beams based on differences in the determined radiation isocenter associated with each of the first, second, and third images.

In some implementations, a fourth image of the seven images is processed to identify an open field, the configuration indicates an open position for the leaves of the MLC, and the operations further include, for each edge in the open field of the fourth image: generating an initial contour based on pixel intensity values of the open field edge; modifying points of the initial contour to minimize internal energy of the contour; moving the points towards the strongest gradient and maintaining regular spacing between the points; and computing a second derivative of the contour to identify corners of the open field edge.

In some implementations, a fifth image of the seven images is processed to detect extended leaves of the MLC, the configuration indicates a first position for a first and second sets of leaves of the MLC, and alternates between indicating second and third positions for a third set of leaves between the first and second sets, and the operations further include: identifying a center of each of the third set of leaves based on an edge of a field in the fifth image; and identifying leaf edges of the third set of leaves.

In some implementations, sixth and seventh of the seven images are processed to detect leaf and jaw positions, for the sixth image, the configuration indicates a first position for a first bank of leaves of the MLC and a second position for a second bank of leaves of the MLC, and for the seventh image, the configuration indicates the first position for a second bank of leaves of the MLC and the second position for a first bank of leaves of the MLC, and the operations further include: generating intensity profiles for the sixth and seventh images; identifying leaf positions based on distances between horizontal centerlines of the field in the sixth and seventh images and the identified leaf edges; and identifying the jaw position based on field edge profiles of the sixth and seventh images.

In some implementations, the selected validation procedure comprises a linear accelerator flatness symmetry validation procedure, wherein the plurality of images include four images obtained at four different gantry angles of the MR-Linac, wherein the characteristic comprises symmetry and flatness of the images, and wherein the allowable threshold comprises a specified percentage value.

In some implementations, the operations, for each image, include: determining location of field edges of the field in the image; computing a mean of the field edge locations to determine the center of the field; generating an average profile from nine vertical profiles, wherein a middle profile of the nine vertical profiles passes through the center of the field; identifying a location of the nine vertical profiles corresponding to 80 percent intensity; determining a difference between first and second of the nine vertical profiles that are equidistant from the middle profile to determine symmetry; and determining variation between values of the nine vertical profiles to determine flatness.

In some embodiments, systems, methods, and computer-readable media are provided for determining image quality of a radiotherapy apparatus comprising an integrated linear accelerator and MRI imaging device (MR-Linac). The systems, methods, and computer-readable media perform operations including: selecting a quality assessment procedure associated with the MRI imaging device of the MR-Linac; obtaining a plurality of images from the MRI imaging device of a phantom that includes at least one module; processing, based on the selected quality assessment procedure, a feature in the plurality of images representing components in the at least one module; computing an image quality attribute associated with the MRI imaging device based on the processed feature; determining whether the image quality attribute satisfies an allowable criterion; and determining whether the MR-Linac is validly operating in response to determining that the image quality attribute satisfies the allowable criterion.

In some implementations, the operations include adjusting one or more characteristics of the MR-Linac in response to determining that the image quality attribute fails to satisfy the allowable criterion.

In some implementations, the quality assessment procedure is a first quality assessment procedure for computing a position of the phantom with respect to axial field of view and computing dimensions of the phantom.

In some implementations, the operations include: selecting a first image of the plurality of images; binarizing the first image such that the phantom shown in the image has a unity pixel value; identifying the column number of the first and last pixel of the phantom in each row of pixels; generating a region of interest (ROI) around the phantom based on the identified column numbers; identifying a center of mass of the ROI based on the identified column numbers; identifying a center of the first image; computing a difference between the coordinates of the phantom and the center of the first image to determine misalignment of the phantom; and computing a height and width of the phantom based on the ROI.

In some implementations, the plurality of quality assessment procedures include at least one of a quality assessment procedure for checking a rotation of the phantom with respect to image space, computing slice thickness accuracy, computing high contrast spatial resolution, checking slice position accuracy, computing percent image uniformity, computing percent signal ghosting, computing low contrast detectability, or computing geometric accuracy.

In some embodiments, systems, methods, and computer-readable media are provided for performing quality assessment of a radiotherapy apparatus comprising an integrated linear accelerator and MRI imaging device (MR-Linac). The systems, methods, and computer-readable media perform operations including: selecting a validation procedure associated with the linear accelerator of the MR-Linac and a quality assessment procedure associated with the MRI imaging device of the MR-Linac; obtaining a first plurality of images from an imaging detector each associated with given radiation beam of a plurality of radiation beams that passes through the MLC that has been adjusted based on the selected validation procedure; obtaining a second plurality of images from the MRI imaging device of a phantom that includes at least one module; processing the first and second plurality of images based on the selected validation and quality assessment procedures; and determining whether the MR-Linac is operating within a valid range based on attributes of the first and second plurality of images determined from processing the first and second plurality of images.

In some implementations, the operations include adjusting one or more characteristics of the MR-Linac in response to determining that the MR-Linac is operating outside of the valid range.

In some implementations, the one or more characteristics are determined based on the selected validation or quality assessment procedure.

The above overview is intended to provide an overview of subject matter of the present patent application. It is not intended to provide an exclusive or exhaustive explanation of the disclosure. The detailed description is included to provide further information about the present patent application.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example but not by way of limitation, various embodiments discussed in the present document.

DETAILED DESCRIPTION

Figure 1:
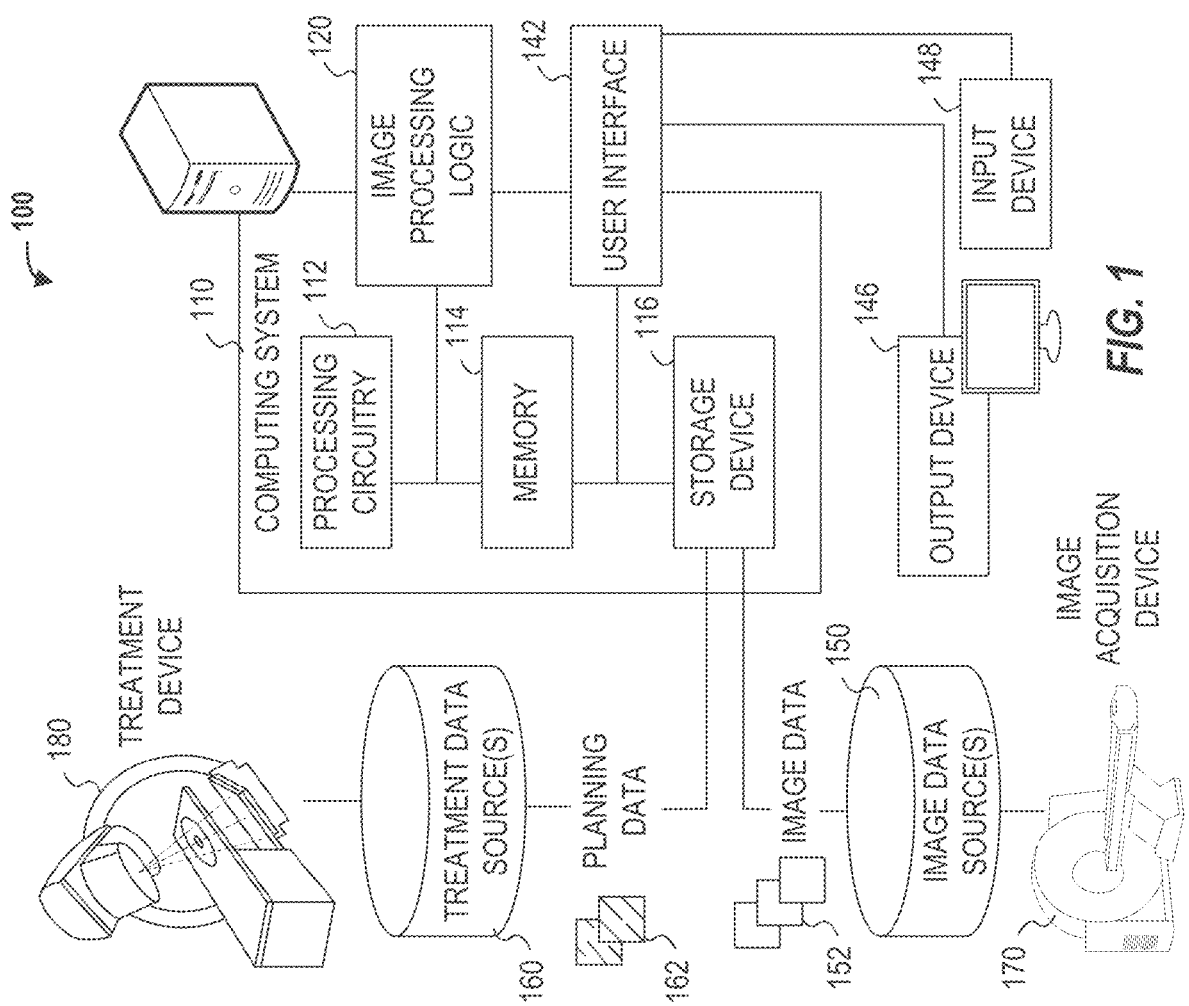
FIG. 1 illustrates an exemplary radiotherapy system adapted for performing treatment plan generation processing according to some examples.

The present disclosure includes techniques that automate quality assurance testing for radiotherapy equipment that includes MR-Linac devices. The present disclosure includes a process for performing a validation procedure for the linear accelerator of the MR-Linac device. The present disclosure includes a process for analyzing quality of the images produced by the MR imaging device of the MR-Linac device. These technical advantages include increased accuracy and consistency between quality assurances testing that is performed across different equipment at different times. These technical advantages reduce downtime of the radiotherapy equipment allowing more patients to be treated. Accordingly, in addition to these technical benefits, the present techniques may also result in many apparent medical treatment benefits (including improved accuracy of radiotherapy treatment, reduced exposure to unintended radiation, and the like).

In some embodiments, the disclosed techniques include web-based tools that analyse 3D images from an MRI imaging device. The techniques are applicable to any MRI imaging device regardless of the particular manufacturer. The disclosed techniques process the images to find the center of mass of a phantom in a set of image files (e.g., DICOM image files) from the MRI imaging device as well as the height and width of the phantom in pixels. The rotation, slice thickness, high contrast spatial resolution, slice position accuracy, percent image uniformity, and percent signal ghosting is determined. Using this information, the accuracy of the MRI imaging device is determined. In some implementations, the height and width of the phantom in pixels is converted to millimetre units. In some embodiments, the rotation of the phantom is determined by analysing the top and bottom on two sides of a black bar in the center of one image. Slice thickness is determined by analysing the brightest portion of several wires in the central portion of the first image.

In some embodiments, the disclosed techniques include vendor agnostic web-based tools that provide quality control for all radiotherapy equipment and imaging equipment. Particularly, the disclosed techniques include web-based tools that can analyse quality and proper performance of a system that has a linear accelerator (Linac) associated with a first manufacturer and a digital imaging panel (detector) associated with a different second manufacturer. For example, a multi-leaf collimator (MLC) leaf position test is provided that enhances the extended leaf detection and subtraction profile in order to support the digital imaging panel. In some implementations, the images produced by the digital imaging panel have different grayscale values than imaging panels provided by the first manufacturer and used by the Linac associated with the first manufacturer. Various image sets with the digital imaging panel are obtained to determine the accurate position of the leaves. An extended leaf detection test is employed that detects leaves that are extended through the field to compute the rotation between the imaging panel and the leaf travel. A subtraction profile test is employed to create a composite image by subtracting two 20×20 centimetre Jaw position detection fields. Particularly, the MLC includes one or more plates above or below the leaves of the MLC that also control the direction and amount of radiation in a given beam. These jaw positions can be determined in the image fields that are detected. A quality assurance is then determined for this radiotherapy equipment that includes components from different manufacturers.

In some embodiments, the disclosed techniques include vendor agnostic web-based tools that provide quality control for an MR-Linac device. Automated quality control tests are provided specific to the MR-Linac (MRL) device. Three image-based tests are provided including an MRL MLC leaf position test, a radiation source and imaging panel (detector) movement test, and an output flatness symmetry versus gantry angle test. In this device, the photon beam characteristics and system geometries are different from conventional Linac systems, which are accounted for in the disclosed quality control tests for the MR-Linac device. In the MRL MLC leaf position test, the MLC leaf position accuracy of 28 leaves is determined. The test takes into account the MR-Linac field size, field characteristics and machine dimensions. In the radiation source and imaging panel (detector) movement test, variations in the location of the radiation source as a function of the gantry angle are detected to detect the 3D location of the megavolt (MV) phantom to determine the maximum displacement of the radiation axis from the mean radiation field centre. A gradient technique is employed for field edge detection. In the output flatness symmetry versus gantry angle test, the analysis of four open field images is performed to determine flatness and symmetry in radial and transverse directions. The output calculated from the central portion of each field is also considered.

FIG. 1 illustrates an exemplary radiotherapy system 100 adapted to perform radiotherapy plan processing operations using one or more of the approaches discussed herein. These radiotherapy plan processing operations are performed to enable the radiotherapy system to provide radiation therapy to a patient based on specific aspects of captured medical imaging data and therapy dose calculations. The radiotherapy system includes a radiotherapy processing computing system 110 which hosts image processing logic 120. The radiotherapy processing computing system 110 may be connected to a network (not shown), and such network may be connected to the Internet. For instance, a network can connect the radiotherapy processing computing system 110 with one or more medical information sources (e.g., a radiology information system (RIS), a medical record system (e.g., an electronic medical record (EMR)/electronic health record (EHR) system), an oncology information system (OIS)), one or more image data sources 150, an image acquisition device 170 (e.g., an imaging modality), a treatment device 180 (e.g., a radiation therapy device), and a treatment data source 160.

The radiotherapy processing computing system 110 may include processing circuitry 112, memory device 114, a storage device 116, and other hardware and software-operable features such as a user interface 142, a communication interface (not shown), and the like. The storage device 116 may store transitory or non-transitory computer-executable instructions, such as an operating system, radiation therapy treatment plans, quality assurance procedures, image quality assessment procedures, validation procedures, software programs (e.g., image processing software, image or anatomical visualization software, AI implementations and algorithms such as provided by DL models, ML models, and neural networks, etc.), and any other computer-executable instructions to be executed by the processing circuitry 112. Processing circuitry 112 may access the instructions stored in storage device 116 to execute and perform any one or more of the quality assurance and validation procedures discussed herein. Processing circuitry 112 may provide a web-tool for an operator to instruct the processing circuitry 112 to perform the quality assurance and validation procedures and the processing circuitry 112 may output and present the results of the quality assurance and validation procedures in graphical or tabulated form to the operator via the web-tool.

Figure 10A:
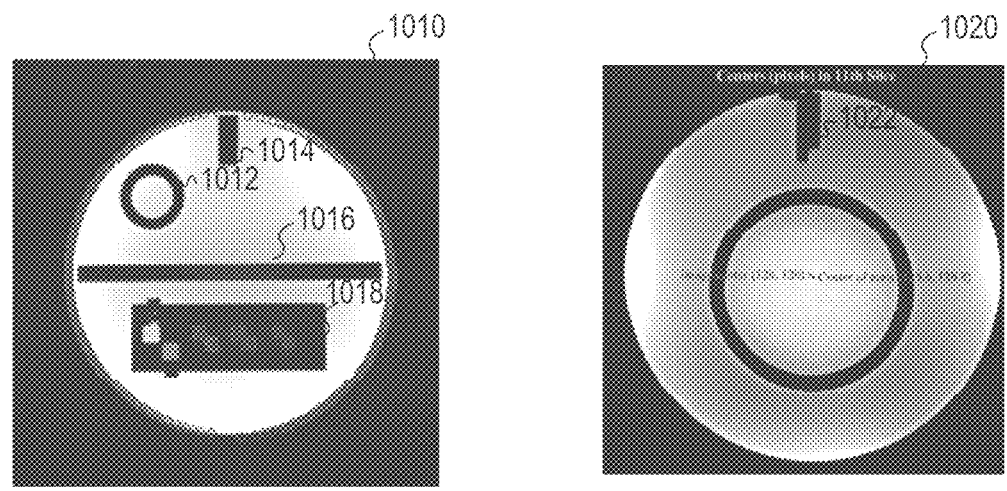
FIGS. 10A and 10B illustrate inputs and outputs of image quality tests of the MRI-Linac device according to some examples of the disclosure.
Figure 10A:
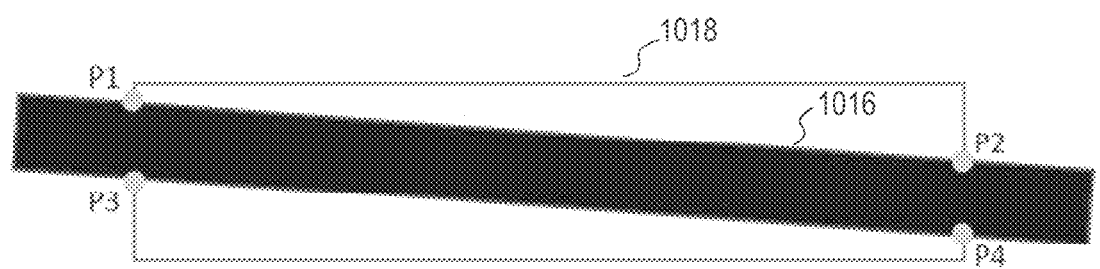
Figure 10A:
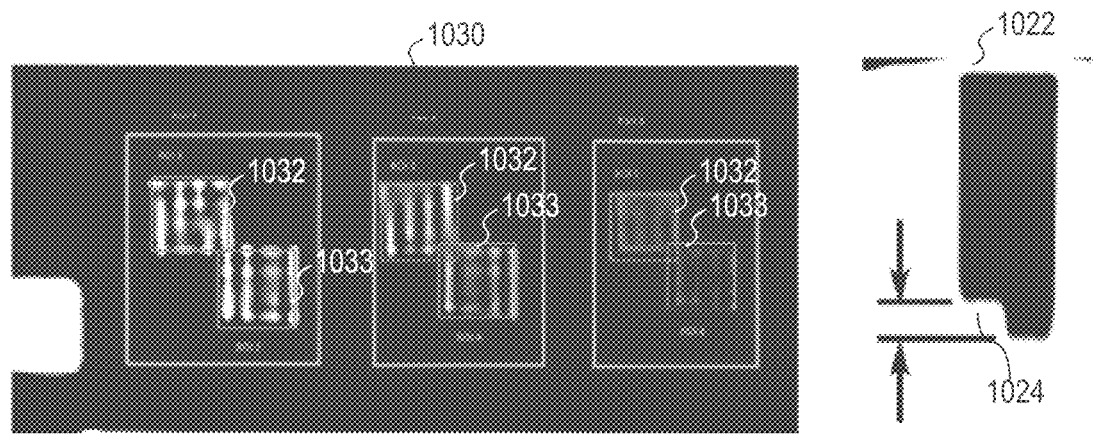
Figure 10B:
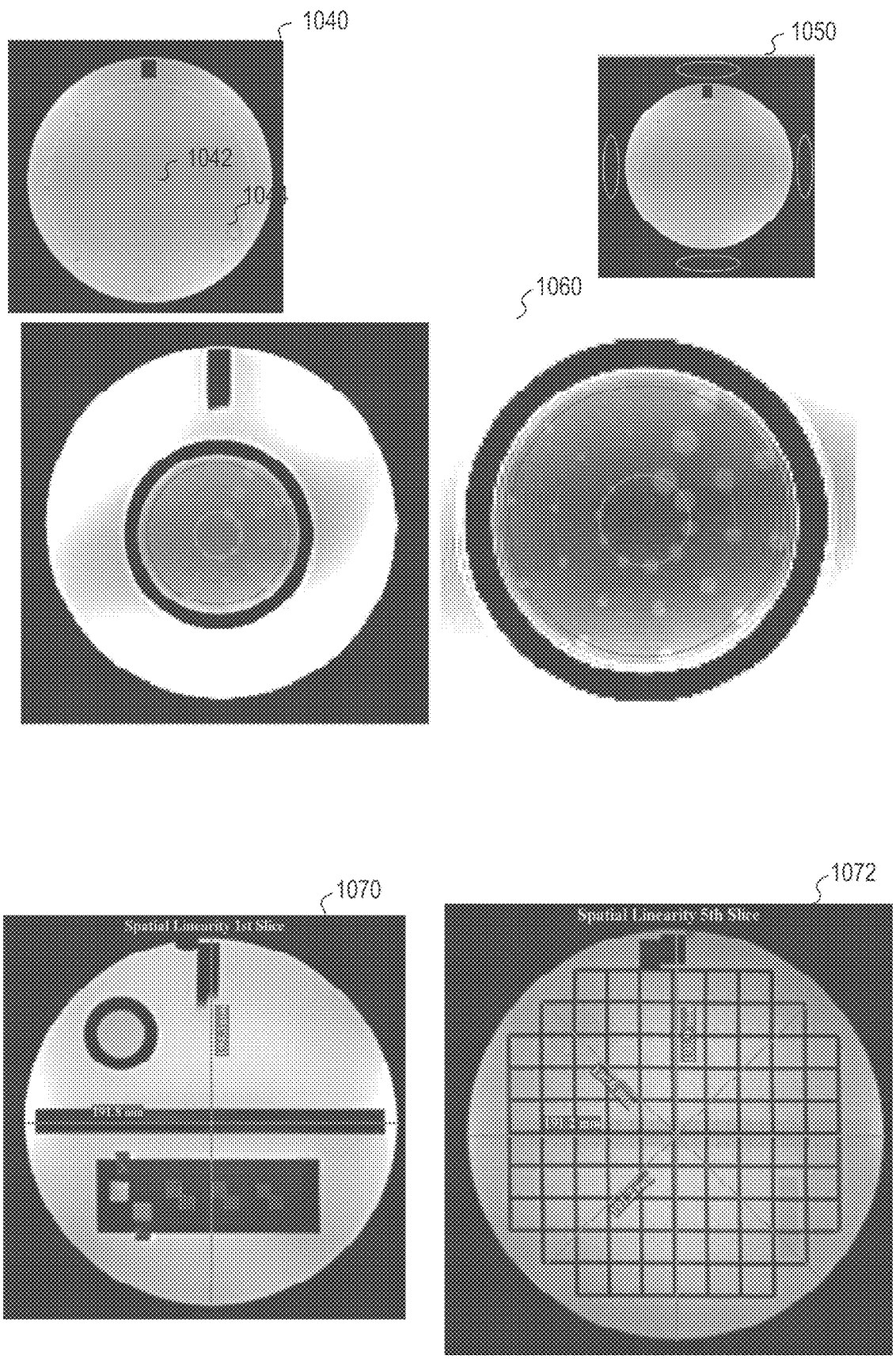
Figure 11:
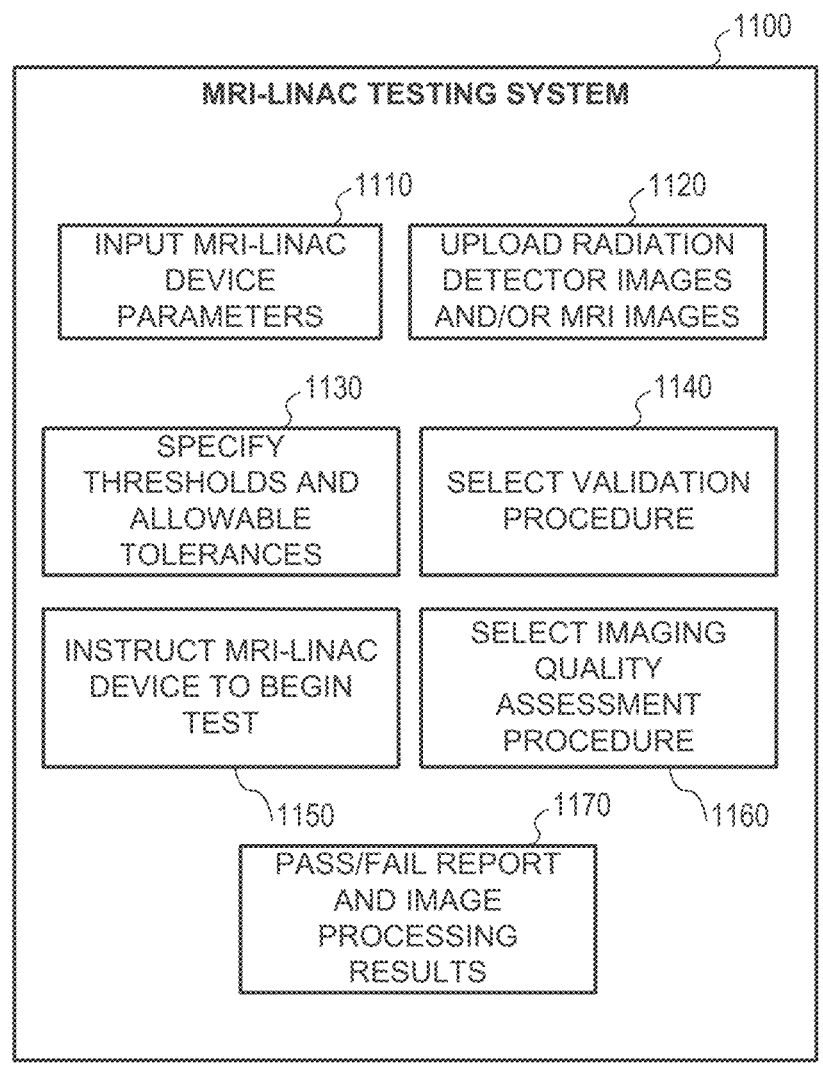
FIG. 11 illustrates an example web-based interface for testing the MRI-Linac device according to some examples of the disclosure.

For example, a user may instruct processing circuitry 112, via a web-tool shown in FIG. 11, to perform any one of a set of quality assurance and validation procedures. After the processing circuitry 112 performs the procedures selected by the user, the outputs the results in the web-tool shown in FIG. 11. In some embodiments, the web-tool shown in FIG. 11 allows a user to input one or more previously captured images of the MRI-Linac device and such images are then processed by the processing circuitry 112 to perform selected quality assurance and validation procedures. In some embodiments, the processing circuitry 112 instructs a user, via the web-tools shown in FIG. 11, on proper placement and positioning of a phantom or other components in connection with testing the MRI-Linac device. After the user configures the MRI-Linac device as instructed by the web-tool, one or more testing images may be captured and processed by the processing circuitry 112 to perform quality assurance and validation procedures. The quality assurance and validation procedures that a user can choose to perform are shown and described in connection with FIGS. 4-10. In some embodiments, the web-tool may inform the user whether any one of a set of the quality assurance and validation procedures passed or failed and may provide a plot or operating range within an allowable operating range of the given MRI-Linac device. In an embodiment, the user can manipulate the allowable thresholds using the web-tool provided in FIG. 11 to configure whether a given MRI-Linac device passes or fails a given quality assurance and validation procedure.

In an example, the processing circuitry 112 may include a processing device, such as one or more general-purpose processing devices such as a microprocessor, a central processing unit (CPU), a graphics processing unit (GPU), an accelerated processing unit (APU), or the like. More particularly, the processing circuitry 112 may be a complex instruction set computing (CISC) microprocessor, a reduced instruction set computing (RISC) microprocessor, a very long instruction Word (VLIW) microprocessor, a processor implementing other instruction sets, or processors implementing a combination of instruction sets. The processing circuitry 112 may also be implemented by one or more special-purpose processing devices such as an application specific integrated circuit (ASIC), a field programmable gate array (FPGA), a digital signal processor (DSP), a System on a Chip (SoC), or the like. As would be appreciated by those skilled in the art, in some examples, the processing circuitry 112 may be a special-purpose processor, rather than a general-purpose processor. The processing circuitry 112 may include one or more known processing devices, such as a microprocessor from the Pentium™, Core™, Xeon™, or Itanium® family manufactured by Intel™, the Turion™, Athlon™, Sempron™ Opteron™, FX™, Phenom™ family manufactured by AMD™, or any of various processors manufactured by Sun Microsystems. The processing circuitry 112 may also include graphical processing units such as a GPU from the GeForce®, Quadro®, Tesla® family manufactured by Nvidia™, GMA, Iris™ family manufactured by Intel™, or the Radeon™ family manufactured by AMD™ The processing circuitry 112 may also include accelerated processing units such as the Xeon Phi™ family manufactured by Intel™. The disclosed embodiments are not limited to any type of processor(s) otherwise configured to meet the computing demands of identifying, analyzing, maintaining, generating, and/or providing large amounts of data or manipulating such data to perform the methods disclosed herein. In addition, the term "processor" may include more than one physical (circuitry based) or software based processor, for example, a multi-core design or a plurality of processors each having a multi-core design. The processing circuitry 112 can execute sequences of transitory or non-transitory computer program instructions, stored in memory device 114, and accessed from the storage device 116, to perform various operations, processes, methods that will be explained in greater detail below. It should be understood that any component in radiotherapy system 100 may be implemented separately and operate as an independent device and may be coupled to any other component in radiotherapy system 100 to perform the techniques described in this disclosure.

The memory device 114 may comprise read-only memory (ROM), a phase-change random access memory (PRAM), a static random access memory (SRAM), a flash memory, a random access memory (RAM), a dynamic random access memory (DRAM) such as synchronous DRAM (SDRAM), an electrically erasable programmable read-only memory (EEPROM), a static memory (e.g., flash memory, flash disk, static random access memory) as well as other types of random access memories, a cache, a register, a compact disc read-only memory (CD-ROM), a digital versatile disc (DVD) or other optical storage, a cassette tape, other magnetic storage device, or any other non-transitory medium that may be used to store information including image, data, or transitory or non-transitory computer executable instructions (e.g., stored in any format) capable of being accessed by the processing circuitry 112, or any other type of computer device. For instance, the computer program instructions can be accessed by the processing circuitry 112, read from the ROM, or any other suitable memory location, and loaded into the RAM for execution by the processing circuitry 112.

The storage device 116 may constitute a drive unit that includes a transitory or non-transitory machine-readable medium on which is stored one or more sets of transitory or non-transitory instructions and data structures (e.g., software) embodying or utilized by any one or more of the methodologies or functions described herein (including, in various examples, the user interface 142). The instructions may also reside, completely or at least partially, within the memory device 114 and/or within the processing circuitry 112 during execution thereof by the radiotherapy processing computing system 110, with the memory device 114 and the processing circuitry 112 also constituting transitory or non-transitory machine-readable media.

The memory device 114 and the storage device 116 may constitute a non-transitory computer-readable medium. For example, the memory device 114 and the storage device 116 may store or load transitory or non-transitory instructions for one or more software applications on the computer-readable medium. Software applications stored or loaded with the memory device 114 and the storage device 116 may include, for example, an operating system for common computer systems as well as for software-controlled devices. The radiotherapy processing computing system 110 may also operate a variety of software programs comprising software code for implementing the image processing logic 120 and the user interface 142. Further, the memory device 114 and the storage device 116 may store or load an entire software application, part of a software application, or code or data that is associated with a software application, which is executable by the processing circuitry 112. In a further example, the memory device 114 and the storage device 116 may store, load, and manipulate one or more radiation therapy treatment plans, imaging data, segmentation data, treatment visualizations, histograms or measurements, AI model data (e.g., weights and parameters), labels and mapping data, and the like. It is contemplated that software programs may be stored not only on the storage device 116 and the memory device 114 but also on a removable computer medium, such as a hard drive, a computer disk, a CD-ROM, a DVD, a Blu-Ray DVD, USB flash drive, a SD card, a memory stick, or any other suitable medium; such software programs may also be communicated or received over a network.

Although not depicted, the radiotherapy processing computing system 110 may include a communication interface, network interface card, and communications circuitry. An example communication interface may include, for example, a network adaptor, a cable connector, a serial connector, a USB connector, a parallel connector, a high-speed data transmission adaptor (e.g., such as fiber, USB 3.0, thunderbolt, and the like), a wireless network adaptor (e.g., such as a IEEE 802.11/Wi-Fi adapter), a telecommunication adapter (e.g., to communicate with 3G, 4G/LTE, and 5G, networks and the like), and the like. Such a communication interface may include one or more digital and/or analog communication devices that permit a machine to communicate with other machines and devices, such as remotely located components, via a network. The network may provide the functionality of a local area network (LAN), a wireless network, a cloud computing environment (e.g., software as a service, platform as a service, infrastructure as a service, etc.), a client-server, a wide area network (WAN), and the like. For example, network may be a LAN or a WAN that may include other systems (including additional image processing computing systems or image-based components associated with medical imaging or radiotherapy operations).

In an example, the radiotherapy processing computing system 110 may obtain image data 152 from the image data source 150 (e.g., MRI images), for hosting on the storage device 116 and the memory device 114. An exemplary image data source 150 is described in detail in connection with FIG. 2. In an example, the software programs operating on the radiotherapy processing computing system 110 may process image data 152 obtained by image data source 150 to perform image quality assessment to provide a quality assurance metric or validation for the radiotherapy equipment. In another example, the software programs operating on the radiotherapy processing computing system 110 may process image data 162 obtained by the treatment device 180 (e.g., a beam detector) to perform a validation procedure to provide a quality assurance metric or validation for the radiotherapy equipment. In an embodiment, a characteristic of the radiotherapy equipment can be adjusted based on the automated quality assessment of the images obtained by the image data source 150 and/or the image data 162 obtained by the treatment device 180.

The processing circuitry 112 may be communicatively coupled to the memory device 114 and the storage device 116, and the processing circuitry 112 may be configured to execute computer executable instructions stored thereon from either the memory device 114 or the storage device 116. The processing circuitry 112 may execute instructions to cause medical images from the image data 152 to be received or obtained in memory device 114 and processed using the image processing logic 120.

In an example, the image data 152 may include one or more MRI image (e.g., 2D MRI, 3D MRI, 2D streaming MRI, 4D MRI, 4D volumetric MRI, 4D cine MRI, etc.), functional MRI images (e.g., fMRI, DCE-MRI, diffusion MRI), Computed Tomography (CT) images (e.g., 2D CT, 2D Cone beam CT, 3D CT, 3D CBCT, 4D CT, 4DCBCT), ultrasound images (e.g., 2D ultrasound, 3D ultrasound, 4D ultrasound), Positron Emission Tomography (PET) images, X-ray images, fluoroscopic images, radiotherapy portal images, Single-Photo Emission Computed Tomography (SPECT) images, computer generated synthetic images (e.g., pseudo-CT images) and the like. Further, the image data 152 may also include or be associated with medical image processing data, for instance, training images, and ground truth images, contoured images, and dose images.

In an example, the image data 152 may be received from the image acquisition device 170 and stored in one or more of the image data sources 150 (e.g., a Picture Archiving and Communication System (PACS), a Vendor Neutral Archive (VNA), a medical record or information system, a data warehouse, etc.). Accordingly, the image acquisition device 170 may comprise a MRI imaging device, a CT imaging device, a PET imaging device, an ultrasound imaging device, a fluoroscopic device, a SPECT imaging device, an integrated Linear Accelerator and MRI imaging device, CBCT imaging device, or other medical imaging devices for obtaining the medical images of the patient. The image data 152 may be received and stored in any type of data or any type of format (e.g., in a Digital Imaging and Communications in Medicine (DICOM) format) that the image acquisition device 170 and the radiotherapy processing computing system 110 may use to perform operations consistent with the disclosed embodiments.

In an example, the image acquisition device 170 may be integrated with the treatment device 180 as a single apparatus (e.g., a MRI device combined with a linear accelerator, also referred to as an "MRI-Linac" or "MR-Linac"). Such an MRI-Linac can be used, for example, to determine a location of a target organ or a target tumor in the patient, so as to direct radiation therapy accurately according to the radiation therapy treatment plan to a predetermined target. For instance, a radiation therapy treatment plan may provide information about a particular radiation dose to be applied to each patient. The radiation therapy treatment plan may also include other radiotherapy information, such as beam angles, dose-histogram-volume information, the number of radiation beams to be used during therapy, the dose per beam, and the like.

The radiotherapy processing computing system 110 may communicate with an external database through a network to send/receive a plurality of various types of data related to image processing and radiotherapy operations. For example, an external database may include machine data (including device constraints) that provides information associated with the treatment device 180, the image acquisition device 170, or other machines relevant to radiotherapy or medical procedures. Machine data information may include radiation beam size, arc placement, beam on and off time duration, machine parameters, segments, multi-leaf collimator (MLC) configuration, gantry speed, MRI pulse sequence, and the like. The external database may be a storage device and may be equipped with appropriate database administration software programs. Further, such databases or data sources may include a plurality of devices or systems located either in a central or a distributed manner.

The radiotherapy processing computing system 110 can collect and obtain data, and communicate with other systems, via a network using one or more communication interfaces, which are communicatively coupled to the processing circuitry 112 and the memory device 114. For instance, a communication interface may provide communication connections between the radiotherapy processing computing system 110 and radiotherapy system components (e.g., permitting the exchange of data with external devices). For instance, the communication interface may, in some examples, have appropriate interfacing circuitry from an output device 146 or an input device 148 to connect to the user interface 142, which may be a hardware keyboard, a keypad, or a touch screen through which a user may input information into the radiotherapy system.

As an example, the output device 146 may include a display device that outputs a representation of the user interface 142 (shown in FIG. 11) and one or more aspects, visualizations, or representations of the medical images, the treatment plans, quality assurance test results, and statuses of training, generation, verification, or implementation of such plans. The output device 146 may include one or more display screens that display medical images, interface information, treatment planning parameters (e.g., contours, dosages, beam angles, labels, maps, etc.), treatment plans, a target, localizing a target and/or tracking a target, or any related information to the user. The input device 148 connected to the user interface 142 may be a keyboard, a keypad, a touch screen or any type of device that a user may input information to the radiotherapy system. Alternatively, the output device 146, the input device 148, and features of the user interface 142 may be integrated into a single device such as a smartphone or tablet computer (e.g., Apple iPad®, Lenovo Thinkpad®, Samsung Galaxy®, etc.).

Furthermore, any and all components of the radiotherapy system may be implemented as a virtual machine (e.g., via VMWare, Hyper-V, and the like virtualization platforms) or independent devices. For instance, a virtual machine can be software that functions as hardware. Therefore, a virtual machine can include at least one or more virtual processors, one or more virtual memories, and one or more virtual communication interfaces that together function as hardware. For example, the radiotherapy processing computing system 110, the image data sources 150, or like components, may be implemented as a virtual machine or within a cloud-based virtualization environment.

The image processing logic 120 or other software programs may cause the computing system to communicate with the image data sources 150 to read images into memory device 114 and the storage device 116, or store images or associated data from the memory device 114 or the storage device 116 to and from the image data sources 150. For example, the image data source 150 may be configured to store and provide a plurality of images (e.g., 3D MRI, 4D MRI, 2D MRI slice images, CT images, 2D Fluoroscopy images, X-ray images, raw data from MR scans or CT scans, Digital Imaging and Communications in Medicine (DICOM) metadata, etc.) that the image data source 150 hosts, from image sets in image data 152 obtained from one or more patients or phantoms via the image acquisition device 170 in performing quality assurance testing. The image data source 150 or other databases may also store data to be used by the image processing logic 120 when executing a software program that performs image processing operations of analyzing quality of the images and performing validation procedures to provide a quality assurance metric or result. The radiotherapy processing computing system 110 thus may obtain and/or receive the image data 152 (e.g., 2D MRI slice images, CT images, 2D Fluoroscopy images, X-ray images, 3DMRI images, 4D MRI images, etc.) from the image data source 150, the image acquisition device 170, the treatment device 180 (e.g., a MRI-Linac), or other information systems, in connection with performing radiation treatment or diagnostic operations.

The image acquisition device 170 can be configured to acquire one or more images of the patient's anatomy for a region of interest (e.g., a target organ, a target tumor or both). Each image, typically a 2D image or slice, can include one or more parameters (e.g., a 2D slice thickness, an orientation, and a location, etc.). In an example, the image acquisition device 170 can acquire a 2D slice in any orientation. For example, an orientation of the 2D slice can include a sagittal orientation, a coronal orientation, or an axial orientation. The processing circuitry 112 can adjust one or more parameters, such as the thickness and/or orientation of the 2D slice, to include the target organ and/or target tumor. In an example, 2D slices can be determined from information such as a 3D CBCT or CT, or MRI volume. Such 2D slices can be acquired by the image acquisition device 170 in "near real-time" while a patient is undergoing radiation therapy treatment, for example, when using the treatment device 180 (with "near real-time" meaning acquiring the data in at least milliseconds or less).

Figure 2:
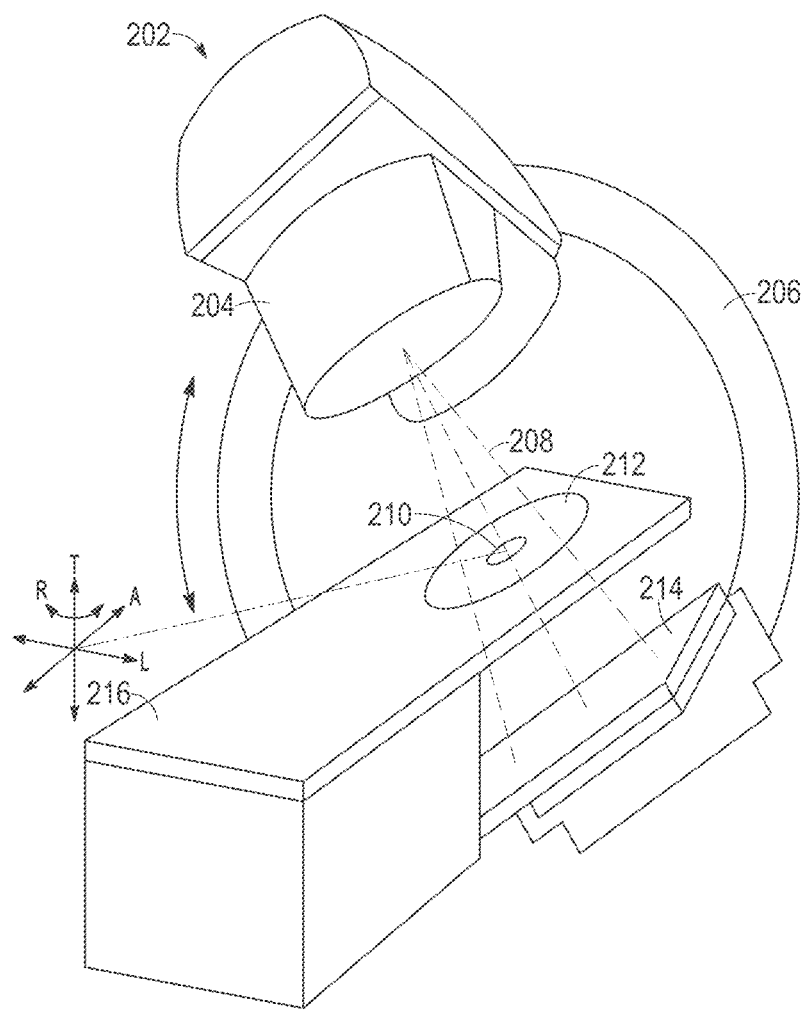
FIG. 2 illustrates exemplary image-guided radiotherapy devices according to some examples of the disclosure.

FIG. 2 illustrates an exemplary image-guided radiation therapy device 202 that includes a radiation source, such as an X-ray source or a linear accelerator, a couch 216, an imaging detector 214, and a radiation therapy output 204. The radiation therapy device 202 may be configured to emit a radiation beam 208 to provide therapy to a patient. The radiation therapy output 204 can include one or more attenuators or collimators, such as a multi-leaf collimator (MLC).

Figure 3:
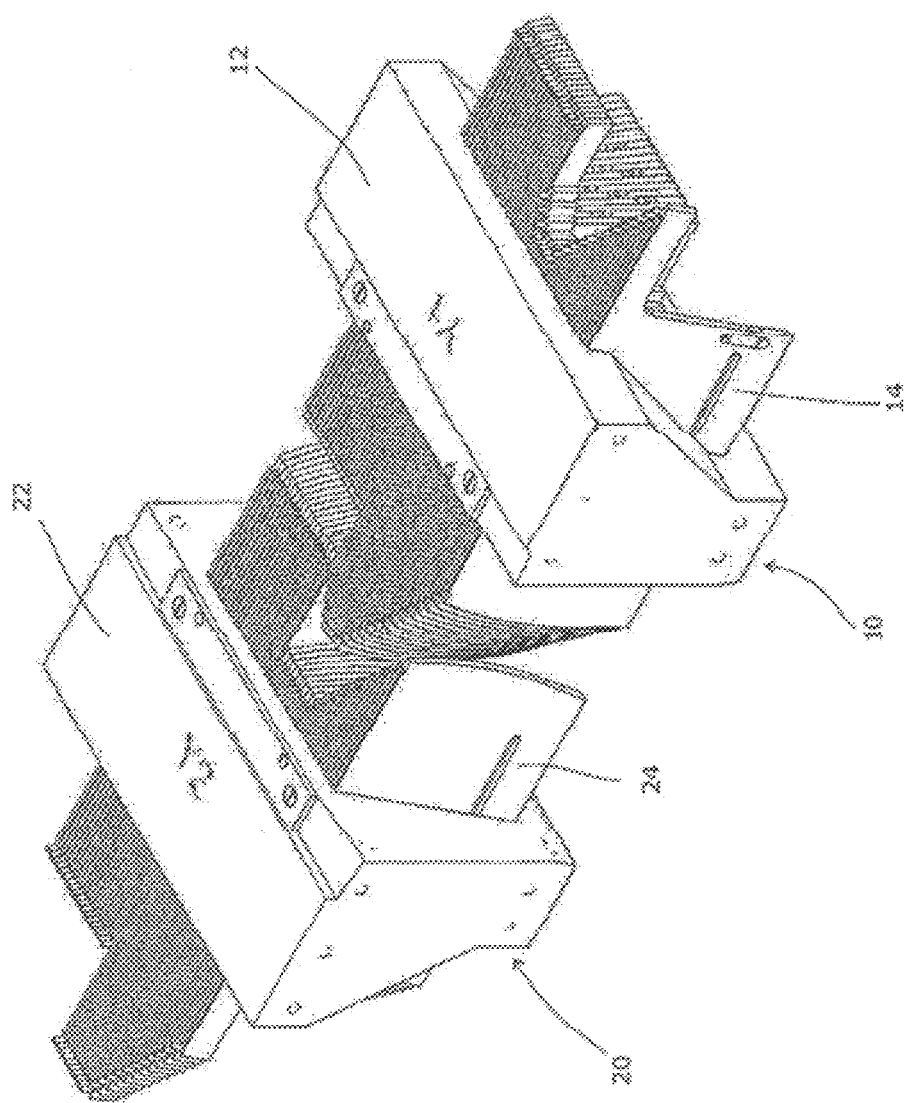
FIG. 3 is a perspective view of a multi-leaf collimator according to some examples of the disclosure.

FIG. 3 shows an MLC according to the present disclosure. Two banks of leaves are provided, each facing the other, one on either side of the beam so as to delimit the beam from opposing sides. Thus, a first bank 10 comprises a frame 12, which supports an array of leaves 14, whilst a second bank 20 comprises a frame 22 which supports an array of leaves 24. Each leaf is oriented in a generally upright manner relative to the beam, with most leaves having a small deflection from perfect verticality as will be described shortly. The leaves 14, 24 are held in the frames 12, 22 by ridges running the length of the upper and lower edges of the leaves, which engage in corresponding channels in the frames so that the leaves can slide horizontally backwards (i.e. out of the beam) and forwards (i.e. into the beam). Each leaf is driven by a suitable motor or other drive means (not illustrated) in a generally known manner.

Referring back to FIG. 2, as an example, a patient can be positioned in a region 212, supported by the treatment couch 216, to receive a radiation therapy dose according to a radiation therapy treatment plan. The radiation therapy output 204 can be mounted or attached to a gantry 206 or other mechanical support. One or more chassis motors (not shown) may rotate the gantry 206 and the radiation therapy output 204 around couch 216 when the couch 216 is inserted into the treatment area. In an example, gantry 206 may be continuously rotatable around couch 216 when the couch 216 is inserted into the treatment area. In another example, gantry 206 may rotate to a predetermined position when the couch 216 is inserted into the treatment area. For example, the gantry 206 can be configured to rotate the therapy output 204 around an axis ("A"). Both the couch 216 and the radiation therapy output 204 can be independently moveable to other positions around the patient, such as moveable in transverse direction ("T"), moveable in a lateral direction ("L"), or as rotation about one or more other axes, such as rotation about a transverse axis (indicated as "R"). A controller communicatively connected to one or more actuators (not shown) may control the couch 216 movements or rotations in order to properly position the patient in or out of the radiation beam 208 according to a radiation therapy treatment plan. Both the couch 216 and the gantry 206 are independently moveable from one another in multiple degrees of freedom, which allows the patient to be positioned such that the radiation beam 208 can precisely target the tumor.

The coordinate system (including axes A, T, and L) shown in FIG. 2 can have an origin located at an isocenter 210. The isocenter can be defined as a location where the central axis of the radiation therapy beam 208 intersects the origin of a coordinate axis, such as to deliver a prescribed radiation dose to a location on or within a patient. Alternatively, the isocenter 210 can be defined as a location where the central axis of the radiation therapy beam 208 intersects the patient for various rotational positions of the radiation therapy output 204 as positioned by the gantry 206 around the axis A.

Gantry 206 may also have an attached imaging detector 214. The imaging detector 214 is preferably located opposite to the radiation source (radiation therapy output 204), and in an example, the imaging detector 214 can be located within a field of the radiation therapy beam 208. Imaging detector 214 may implement image-processing logic 120 (FIG. 1) to generate images for conducting validation procedure testing in real time. The imaging detector 214 can be mounted on the gantry 206, preferably opposite the radiation therapy output 204, such as to maintain alignment with the radiation therapy beam 208. The imaging detector 214 rotates about the rotational axis as the gantry 206 rotates. In an example, the imaging detector 214 can be a flat panel detector (e.g., a direct detector or a scintillator detector). In this manner, the imaging detector 214 can be used to monitor the radiation therapy beam 208, or the imaging detector 214 can be used for imaging the patient's anatomy, such as portal imaging.

The control circuitry of radiation therapy device 202 may be integrated within the radiotherapy system 100 or remote from it.

In an illustrative example, one or more of the couch 216, the therapy output 204, or the gantry 206 can be automatically positioned, and the therapy output 204 can establish the radiation therapy beam 208 according to a specified dose for a particular therapy delivery instance. A sequence of therapy deliveries can be specified according to a radiation therapy treatment plan, such as using one or more different orientations or locations of the gantry 206, couch 216, or therapy output 204. The therapy deliveries can occur sequentially, but can intersect in a desired therapy locus on or within the patient, such as at the isocenter 210. A prescribed cumulative dose of radiation therapy can thereby be delivered to the therapy locus while damage to tissue nearby the therapy locus can be reduced or avoided.

Thus, FIG. 2 specifically illustrates an example of a radiation therapy device 202 operable to provide radiotherapy treatment to a patient, with a configuration where a radiation therapy output can be rotated around a central axis (e.g., an axis "A"). Other radiation therapy output configurations can be used. For example, a radiation therapy output can be mounted to a robotic arm or manipulator having multiple degrees of freedom. In yet another example, the therapy output can be fixed, such as located in a region laterally separated from the patient, and a platform supporting the patient can be used to align a radiation therapy isocenter with a specified target locus within the patient. In another example, a radiation therapy device can be a combination of a linear accelerator and an image acquisition device. In some examples, the image acquisition device may be an MRI, an X-ray, a CT, a CBCT, a spiral CT, a PET, a SPECT, an optical tomography, a fluorescence imaging, ultrasound imaging, or radiotherapy portal imaging device, etc., as would be recognized by one of ordinary skill in the art.

In certain embodiments, a phantom is used to assess the image quality of the MRI imaging device of the MR-Linac device. Namely, a registration process is used to identify any rotation in the coordinate space to verify the successful application of predetermined region-of-interest processing. To assess the image quality, identifiable targets in commercially available phantoms can be determined. Such an MRI phantom has a number of circular inserts spaced radially around the axis of a cylindrical volume. Each insert has a number of vanes or target pins spaced so as to simulate a different spatial frequency. The unknown in such an acquired image will be the angular rotation of the cylinder. An object to be used for registration is embedded in the plane of the volume of interest, which has a structure that is significantly different from the test objects. For instance, if the test patterns utilize circular elements, then the registration target is a rectangular (or at least rectilinear) object. It should also be a size or density difference so that when an appropriate pixel value or morphological (shape sensitive) filter is applied to the resulting image, a clear discrimination between the registration target and the test features is obtained. Once the pixel coordinates of the registration target have been determined, then the orientation of the test features can be derived using a priori knowledge of the spatial relationship between all of the features in the phantom.

In some embodiments, a user may select a validation procedure to perform that tests the MLC leaf and jaw positions. This validation procedure uses seven electronic portal imaging device (EPID) images of an MRI-Linac device of various MLC and jaw defined field patterns. Each image of the seven EPID images is captured after a corresponding beam of radiation is passed through the MLC leaves and jaw in a given configuration.

The objective of this validation procedure is to determine the MLC leaf position accuracy of the central 28 leaves at two nominal locations. In such cases, the processing circuitry 112 detects the leaf and jaw positions and indicates if there are any errors associated with the positions. In some cases, the processing circuitry 112 generates and reports a summation profile of two picket images with an approximate guideline for 0.5 mm and 1 mm leaf gaps. In some implementations, the processing circuitry 112 outputs a mean radiation isocenter (using the first three images of the seven) and a location of the PEID reference pixel. The processing circuitry 112 may also output the MLC leaf positions for the central 30 leaves in each bank (where there are 60 leaves total) at two nominal locations. The processing circuitry 112 may also output plot views of the test including an MLC leaf position versus leaf number plot, parameter versus parameter plot, and/or mean radiation isocenter x & y coordinates trended over time plot.

In an embodiment, to start this validation procedure, an operator, via the web-tools shown in FIG. 11, inputs parameters that define the MRI-Linac device being tested and optionally inputs testing parameters. After the user inputs an instruction to begin the validation procedure, the processing circuitry 112 performs the process described in connection with FIGS. 4A and 4B to verify proper operation and alignment of the MLC leaf and jaw positions.

Figure 4A:
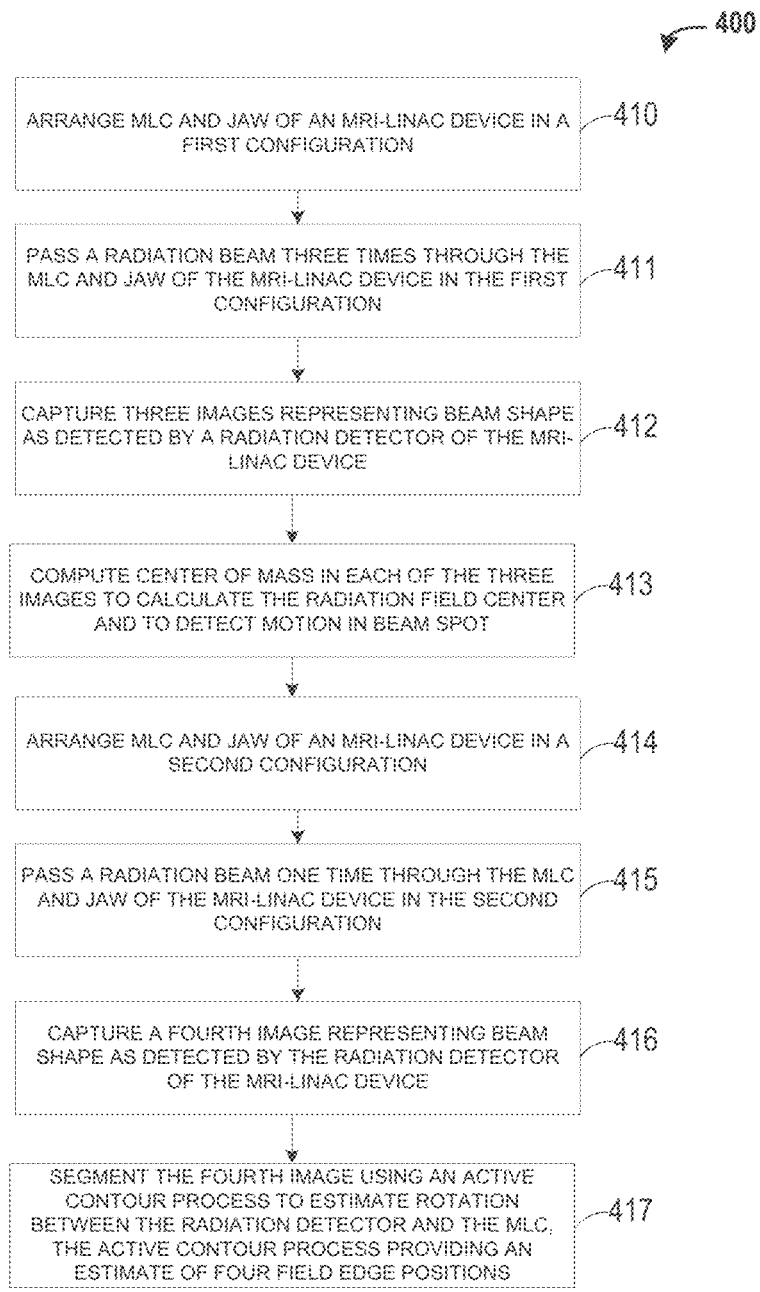
FIGS. 4A and 4B provide an illustrative process for testing an MLC and Jaw configuration of an MRI-Linac device according to some examples of the disclosure.
Figure 4B:
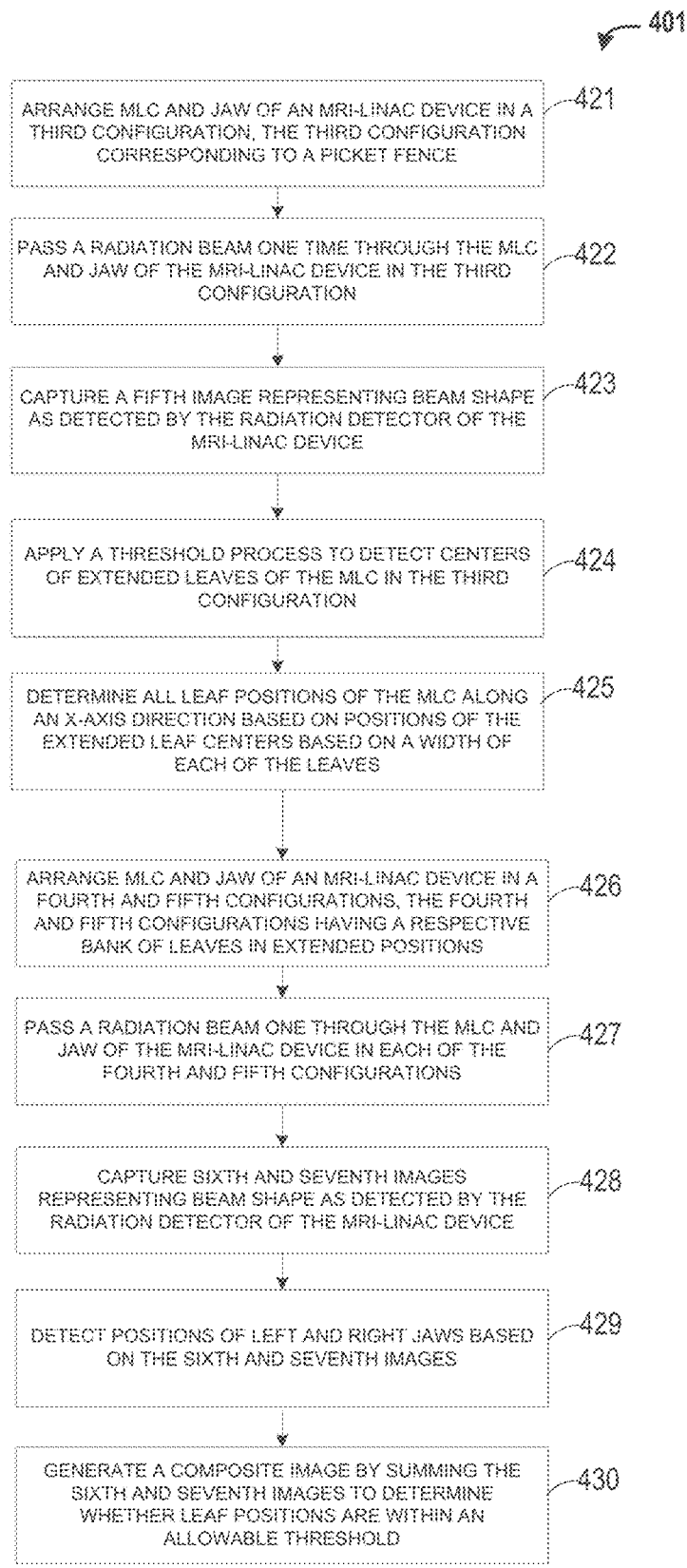

FIGS. 4A and 4B provide an illustrative process for testing an MLC and Jaw configuration of an MRI-Linac device according to some examples of the disclosure. Specifically, FIGS. 4A and 4B are flowcharts illustrating example operations of the image processing logic 120 in performing processes 400 and 401, according to example embodiments. The processes 400 and 401 may be embodied in computer-readable instructions for execution by one or more processors such that the operations of the processes 400 and 401 may be performed in part or in whole by the functional components of the image processing logic 120; accordingly, the processes 400 and 401 is described below by way of example with reference thereto. However, in other embodiments, at least some of the operations of the processes 400 and 401 may be deployed on various other hardware configurations. The processes 400 and 401 are therefore not intended to be limited to the image processing logic 120 and can be implemented in whole, or in part, by any other component. Some or all of the operations of processes 400 and 401 can be in parallel, out of order, or entirely omitted.

In an embodiment, the validation procedure for the MLC leaf and jaw positions, the processing circuitry 112 uses three images of a 4×4 cm field that is acquired to estimate the location of the mean radiation field center in the flat panel plane. An iterative thresholding technique is used to separate the image grayscale histogram into two regions. The two regions are used to segment the open field in each image. The center of the segmented region is determined based on a center of mass calculation. A circular function is fit to the calculated centroids and the center of the circular fit is taken as the mean field center.

Specifically, at operation 410, the image processing logic 120 (e.g., using processing circuitry 112) arranges the MLC and jaw of the MRI-Linac device in a first configuration. For example, to estimate the location of the mean radiation field center, the image processing logic arranges the MLC and jaw of the MRI-Linac device so that a small open field is defined by the MLC only. The x jaws are parked at 10 cm on each side. The side of the leaves create the field edge in the x direction. This may eliminate the impact of the jaw calibration on the variation of the radiation beam axis position. If there is motion of the radiation beam axis in the x direction as a function of time, this could indicate a change in the MLC bank position with respect to the beam source.

At operation 411, the image processing logic 120 passes a radiation beam three times through the MLC and jaw of the MRI-Linac device in the first configuration. As shown in Tables 1 and 2 below, the first configuration of the jaws and the MLC leaf positions for each of the three radiation beams is defined:

TABLE 1

Jaw positions and gantry angle for the MLC leaf and jaw positions validation procedure

| Beam Number | Field Size (cm) | | | | Gantry Angle Deg |
| --- | --- | --- | --- | --- | --- |
| | X1 | X2 | Y1 | Y2 | |
| 1 | 10 | 10 | 2 | 2 | 0 |
| 2 | 10 | 10 | 2 | 2 | 0 |
| 3 | 10 | 10 | 2 | 2 | 0 |

TABLE 2

MLC leaf positions for the first three beams in the MLC leaf and jaw positions validation procedure

| Leaf number | Top bank-Leaf position (cm) | Bottom bank-Leaf position (cm) |
| --- | --- | --- |
| 1 to 37 | −11 | 11 |
| 38 | 2 | 2 |
| 39 | 2 | 2 |
| 40 | 2 | 2 |
| 41 | 2 | 2 |
| 42 | 2 | 2 |
| 43 | 2 | 2 |
| 44 to 80 | −11 | 11 |

Figure 5:
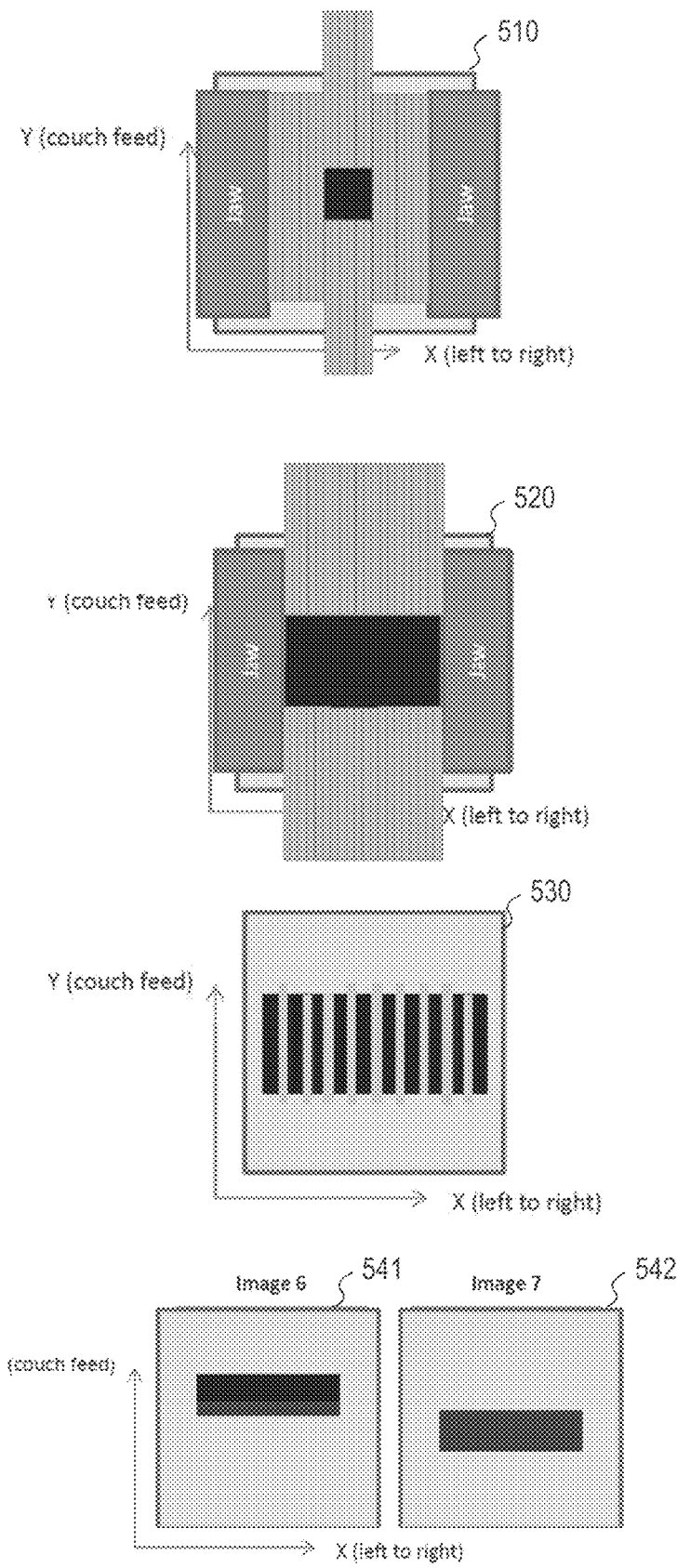
FIG. 5 illustrates inputs and outputs of the MLC and Jaw configuration test of the MRI-Linac device according to some examples of the disclosure.

At operation 412, the image processing logic 120 captures three images representing beam shape as detected by a radiation detector of the MRI-Linac device while the MRI-Linac is in the first configuration 510. FIG. 5 shows a resulting one of the three images of the first configuration 510 of the jaw and MLC leaf positions of the MRI-Linac device for the three beams in the MLC leaf and jaw positions validation procedure. First configuration 510 enables the image processing logic 120 to estimate the location of the mean radiation field center by arranging the MLC and jaw of the MRI-Linac device so that a small open field is defined by the MLC only (represented as the black rectangular square in the middle of the first configuration 510).

At operation 413, the image processing logic 120 computes a center of mass in each of the three images to calculate the radiation field center and to detect motion in the beam spot. Specifically, the image processing logic 120, for each of the three images generated when the MLC and leaf positions are in the first configuration, segments the open field portion of the images using an iterative threshold technique. The image processing logic 120 computes a center of mass to determine the radiation field center (mean isocentre) and repeats this analysis for the three images to determine if there are any motions in the beam spot. If motion is detected, an indication is provided to the user in the web-tool (e.g., by indicating that this validation procedure failed). In an implementation, by delimiting the field in the x direction using the MLC leaves, the location of the radiation axis in the x direction may exactly coincide with the junction between leaves 40 and 41.

At operation 414, the image processing logic 120 arranges the MLC and jaw of the MRI-Linac device in a second configuration. For example, the processing circuitry 112 uses an 8×20 cm² open field for a first detection of the MLC and jaw position.

At operation 415, the image processing logic 120 passes a radiation beam one time through the MLC and jaw of the MRI-Linac device in the second configuration. As shown in Table 3 below, the second configuration of the jaws and the MLC leaf positions for the radiation beam is defined:

TABLE 3

MLC leaf positions for the fourth beam in the
MLC leaf and jaw positions validation procedure

| Beam | Field Size (cm) | | | | Gantry Angle | MLC |
|---|---|---|---|---|---|---|
| Number | X1 | X2 | Y1 | Y2 | Deg | Positions |
| 4 | 10 | 10 | 4 | 4 | 0 | N/A |

At operation 416, the image processing logic 120 captures a fourth image representing beam shape as detected by the radiation detector of the MRI-Linac device. FIG. 5 shows the resulting images of the second configuration 520 of the jaw and MLC leaf positions of the MRI-Linac device for the fourth beam in the MLC leaf and jaw positions validation procedure. The second configuration 520 enables the image processing logic 120 to estimate the four field edge positions and estimate rotation between the panel and the collimator. The rotation between the MLC and the panel may be determined and compared to a geometry file specifying an expected rotation to determine whether or not rotation of the system has changed over time.

At operation 417, the image processing logic 120 segments the fourth image using an active contour process to estimate rotation between the radiation detector and the MLC. The active contour process providing an estimate of four field edge positions. Specifically, the image processing stops if the field is truncated or if the field edge is within 3 mm of the image edge. The active contour process iteratively modifies points of an initial contour to minimize the internal energy of the contour (represented by the continuity and the curvature of the contour) and the image force (represented by the image gradient). During the iterative process, the process moves the contour points toward the strongest gradient while minimizing the contour's curvature and maintaining regular spacing between the points. In the final solution, the points for which the second derivative of the contour exceeds a set threshold are identified as the field corners. Once the field corners are located, the remaining contour points can be grouped by field edge. The point on a given field edge is used to parameterize the field edge using a linear equation. This process is repeated for the four field borders.

At operation 421, continued in FIG. 4B, the image processing logic 120 arranges the MLC and jaw of the MRI-Linac device in a third configuration corresponding to a picket fence. For example, the processing circuitry 112 uses a 8×20 cm² with extended leaf pattern with leaves crossing the isocentre to compute the rotation between the flat panel and the leaf travel.

At operation 422, the image processing logic 120 passes a radiation beam one time through the MLC and jaw of the MRI-Linac device in the third configuration. As shown in Tables 4 and 5 below, the third configuration of the jaws and the MLC leaf positions for the radiation beam is defined:

TABLE 4

Jaw positions and gantry angle for the MLC
leaf and jaw positions validation procedure

| Beam | Field Size | | | | Gantry |
|---|---|---|---|---|---|
| Number | X1 | X2 | Y1 | Y2 | Angle |
| 5 | 10 | 10 | 4 | 4 | 0 |

TABLE 5

MLC leaf positions for the fifth beam in the MLC
leaf and jaw positions validation procedure

| Leaf number | Top bank-Leaf position (cm) | Bottom bank-Leaf position (cm) |
|---|---|---|
| 1 to 26 | −11 | 11 |
| 27 | −5 | 5 |
| 28 | 4 | 4 |
| 29 | 5 | −5 |
| 30 | 4 | 4 |
| 31 | −5 | 5 |
| 32 | 4 | 4 |
| 33 | 5 | −5 |
| 34 | 4 | 4 |
| 35 | −5 | 5 |
| 36 | 4 | 4 |
| 37 | 5 | −5 |
| 38 | 4 | 4 |
| 39 | −5 | 5 |
| 40 | 4 | 4 |
| 41 | 5 | −5 |
| 42 | 4 | 4 |
| 43 | −5 | 5 |
| 44 | 4 | 4 |
| 45 | 5 | −5 |
| 46 | 4 | 4 |
| 47 | −5 | 5 |
| 48 | 4 | 4 |
| 49 | 5 | −5 |
| 50 | 4 | 4 |
| 51 | −5 | 5 |
| 52 | 4 | 4 |
| 53 | 5 | −5 |
| 54 | 4 | 4 |
| 55 to 80 | −11 | 11 |

At operation 423, the image processing logic 120 captures a fifth image representing beam shape as detected by the radiation detector of the MRI-Linac device. FIG. 5 shows the resulting images of the third configuration 530 of the jaw and MLC leaf positions of the MRI-Linac device for the fifth beam in the MLC leaf and jaw positions validation procedure. The third configuration 530 enables the image processing logic 120 to compute the rotation between the flat panel and the leaf travel.

The extended leaf centers in the images are detected using the Otsu's method. The positions of the extended leave centers are then used to determine all leaf positions in the x axis direction, such as using a width of the leaves. The extended leaf pattern also provides the rotation between the MLC and the flat panel which can be compared to a predetermined expected rotation that is previously stored. Specifically, the extended leaf pattern may indicate rotation if an angle exists in the fence or leaf pattern that is captured in the image.

At operation 424, the image processing logic 120 applies a threshold process to detect centers of extended leaves of the MLC in the third configuration.

At operation 425, the image processing logic 120 determines all leaf positions of the MLC along an x-axis direction based on positions of the extended leaf centers based on a width of each of the leaves. For example, the image processing logic 120 determines the center of each extended leaf by starting from the edge of the field and expecting 28 visible leaves in the field. Namely, the image processing logic 120 may detect the edge of the black box generated from the third configuration 530 and identifies 28 leaves between the edges until the opposite edge. The image processing logic 120 draws perpendicular profiles along the leaf directions and their maximum gradient indicates the leaf edge. The mean angle between the detected extended leaves and the imager's rows is calculated and the linear equation of the field centreline perpendicular to the leaf path and passing by the radiation isocentre is obtained. Based on this angle, the image processing logic determines the rotation between the MLC and the flat panel and determines whether such a rotation is within allowable thresholds or matches an expected rotation.

At operation 426, the image processing logic 120 arranges the MLC and jaw of the MRI-Linac device in a fourth and fifth configuration, the fourth and fifth configurations having a respective bank of leaves in extended positions. For example, the processing circuitry 112 uses a 4×20 cm² configuration with two abutting pickets to determine whether the leaf positions are in or out of allowable thresholds or specifications.

At operation 427, the image processing logic 120 passes a radiation beam one time through the MLC and jaw of the MRI-Linac device in each of the fourth and fifth configurations. As shown in Tables 6 and 7 below, the fourth and fifth configurations of the jaws and the MLC leaf positions for the radiation beam is defined:

TABLE 6

Jaw positions and gantry angle for the MLC leaf and jaw positions validation procedure

| Beam Number | Field Size (cm) | | | | Gantry Angle |
|---|---|---|---|---|---|
| | X1 | X2 | Y1 (Top) | Y2 (Bottom) | |
| 6 | 10 | 10 | 4 | 0 | 0 |
| 7 | 10 | 10 | 0 | 4 | 0 |

TABLE 7

MLC leaf positions for the sixth and seventh beam in the MLC leaf and jaw positions validation procedure

| Leaf number | Y1 Top bank- Leaf position (cm) | Y2 Bottom bank- Leaf position (cm) |
|---|---|---|
| MLC Leaf Positions for Image 6 | | |
| 1 to 26 | 0 | 0 |
| 27 | 4 | 0 |
| 28 | 4 | 0 |
| 29 | 4 | 0 |
| 30 | 4 | 0 |
| 31 | 4 | 0 |
| 32 | 4 | 0 |
| 33 | 4 | 0 |
| 34 | 4 | 0 |
| 35 | 4 | 0 |
| 36 | 4 | 0 |
| 37 | 4 | 0 |
| 38 | 4 | 0 |
| 39 | 4 | 0 |
| 40 | 4 | 0 |
| 41 | 4 | 0 |
| 42 | 4 | 0 |
| 43 | 4 | 0 |
| 44 | 4 | 0 |
| 45 | 4 | 0 |
| 46 | 4 | 0 |
| 47 | 4 | 0 |
| 48 | 4 | 0 |
| 49 | 4 | 0 |
| 50 | 4 | 0 |
| 51 | 4 | 0 |
| 52 | 4 | 0 |
| 53 | 4 | 0 |
| 54 | 4 | 0 |
| 55 to 80 | 0 | 0 |
| MLC Leaf Positions for Image 7 | | |
| 1 to 26 | 0 | 0 |
| 27 | 0 | 4 |
| 28 | 0 | 4 |
| 29 | 0 | 4 |
| 30 | 0 | 4 |
| 31 | 0 | 4 |
| 32 | 0 | 4 |
| 33 | 0 | 4 |
| 34 | 0 | 4 |
| 35 | 0 | 4 |
| 36 | 0 | 4 |
| 37 | 0 | 4 |
| 38 | 0 | 4 |
| 39 | 0 | 4 |
| 40 | 0 | 4 |
| 41 | 0 | 4 |
| 42 | 0 | 4 |
| 43 | 0 | 4 |
| 44 | 0 | 4 |
| 45 | 0 | 4 |
| 46 | 0 | 4 |
| 47 | 0 | 4 |
| 48 | 0 | 4 |
| 49 | 0 | 4 |
| 50 | 0 | 4 |
| 51 | 0 | 4 |
| 52 | 0 | 4 |
| 53 | 0 | 4 |
| 54 | 0 | 4 |
| 55 to 80 | 0 | 0 |

At operation 428, the image processing logic 120 captures sixth and seventh images representing beam shape as detected by the radiation detector of the MRI-Linac device. FIG. 5 shows the resulting images of the fourth and fifth configurations 541 and 542, respectively, of the jaw and MLC leaf positions of the MRI-Linac device for the sixth and seventh beams in the MLC leaf and jaw positions validation procedure.

At operation 429, the image processing logic 120 detects positions of left and right jaws based on the sixth and seventh images. For example, the image processing logic 120 detects leaf positions for all visible leaves in the field of view for two different leaf positions seen in the two different pickets (shown in the resulting images of the fourth and fifth configurations 541 and 542). The image processing logic 120 extracts intensity profiles perpendicular to the horizontal field centreline under each leaf and normalizes the profiles to their maximum open field value. Individual leaf positions are calculated along the extracted profiles as the distance between the horizontal field centreline and the leaf edge (as determined from operation 425). The leaf edge is identified using a predefined penumbra detection level that may be specified using the web-tool or hard coded into the system. The leaf positions are converted to millimeters using a pixel-scaling factor. The image processing logic 120 detects the position of the left and right jaws by analysing the 20×8 $cm^2$ field. The jaws are at nominal position of 0 cm and 20 cm. A maximum gradient method is used to determine the location of the field edge. The image processing logic 120 analyzes the gradients of 11 profiles spanning the field edge per field edge. The location of the field edge is determined by averaging the result of the maximum gradient method for these 11 profiles.

In some embodiments, the image processing logic 120 presents the results of the previous operations in two different tables for the Y1 and Y2 MLC leaf banks. The measured position of each leaf at each of the two picket positions may be indicated. In an embodiment, the validation procedure passes the test if all of the measured leaf positions are within 1 mm of the nominal leaf positions. In some embodiments, leaf positions that are outside of this range may be indicated in a red in the tables. The image processing logic 120 uses the open field image to determine the position of the x jaws (left and right jaws). The overall test results may be presented and the test passes if the jaw positions are within 1 mm of the nominal jaw position. In some embodiments, jaw positions that are outside of this range may be indicated in a red in the tables.

At operation 430, the image processing logic 120 generates a composite image by summing the sixth and seventh images to determine whether leaf positions are within an allowable threshold. For example, the profiles may be taken under each leaf across the two pickets (shown in the resulting images of the fourth and fifth configurations 541 and 542) and averaged in order to provide a normalization basis. The height of the peaks and valleys at the field junctions depend on the leaf gap at the field junction. The tolerance lines on the plot may serve as an approximate guideline for the 0.5 mm and 1 mm leaf gaps. This plot may provide a visual verification of the tabulated results. In some cases, if the profile peak exceeds a tolerance line, the corresponding leaf position may be indicated as being out of the 1 mm tolerance in the tabulated results.

FIGS. 6-9 provide illustrative processes for testing an MRI-Linac device according to some examples of the disclosure. Specifically, FIGS. 6-9 are flowcharts illustrating example operations of the image processing logic 120 in performing processes 600-900, according to example embodiments. The processes 600-900 may be embodied in computer-readable instructions for execution by one or more processors such that the operations of the processes 600-900 may be performed in part or in whole by the functional components of the image processing logic 120; accordingly, the processes 600-900 is described below by way of example with reference thereto. However, in other embodiments, at least some of the operations of the processes 600-900 may be deployed on various other hardware configurations. The processes 600-900 are therefore not intended to be limited to the image processing logic 120 and can be implemented in whole, or in part, by any other component. Some or all of the operations of processes 600-900 can be in parallel, out of order, or entirely omitted.

In some embodiments, a user may select a validation procedure to perform that tests the radiation source and EPID movement as a function of the gantry angle using an MV geometry phantom. This validation procedure uses 8 images of the MV phantom captured at 8 different gantry angles using an 8×8 cm field. In some cases, the phantom includes a ball bearing (BB) located at the isocenter. The 8 images are acquired at gantry angles of 180 degrees, 135 degrees, 90 degrees, 45 degrees, 0 degrees, −45 degrees, −90 degrees, and −135 degrees. Any other suitable additional or different angles may be used similarly.

The objective of this validation procedure is to detect and report variations in the location of the radiation source and the EPID reference pixel as a function of gantry angle. Also, the 3D location of the phantom is detected and reported and a maximum displacement of the radiation axis from the mean radiation field center is reported to a user. In an embodiment, the web-tool shown in FIG. 11 outputs the central ball bearing position in 3D space and the maximum displacement of the radiation axis from the mean radiation isocenter. The test also outputs, perpendicular to the axis of rotation: the location of the x reference pixel, the displacement of the radiation axis from the radiation isocenter at each angle, and the constancy of mean radiation axis with respect to the x reference pixel (sensitive to changes in the MLC leaf bank position). The test also outputs, parallel to the axis of rotation: the location of the y reference pixel and the constancy of mean radiation isocenter with respect to the reference pixel (sensitive to changes in mechanical alignment and asymmetrical changes in the MLC leaf bank alignment. In some cases, a plot is generated and provided to the user that illustrates the ball bearing center coordinates versus the gantry angle. The reference pixel is determined prior to the test (e.g., when the MRI-Linac device is installed) in the megavolt (MV) panel coordinate system that corresponds to the mean isocenter of the MRI-Linac device.

In an embodiment, to start this validation procedure, an operator, via the web-tools shown in FIG. 11, inputs parameters that define the MRI-Linac device being tested and optionally inputs testing parameters. After the user inputs an instruction to begin the validation procedure, the processing circuitry 112 performs the process described in connection with FIG. 6 to verify the radiation source and EPID movement.

Specifically, at operation 601, the image processing logic 120 passes a radiation beam eight times through a phantom positioned within an isocentre of an MRI-Linac device at eight different gantry angles.

At operation 602, the image processing logic 120 captures eight images of the phantom representing beam shape as detected by the radiation detector of the MRI-Linac device for each of the eight radiation beams. In some cases, the images are loaded from storage as they may have previously been captured and provided to the image processing logic 120. As shown in Table 8 below, the configuration of the jaws and the MLC leaf positions and the gantry angle for each of the eight radiation beams is defined:

TABLE 8

Jaw and leaf positions and gantry angle for the radiation source and EPID movement validation procedure

| Beam | Field size (cm) | | | | Gantry angle |
|---|---|---|---|---|---|
| number | X1 | X2 | Y1 | Y2 | Deg |
| 1 | 10 | 10 | 4 | 4 | 180 |
| 2 | 10 | 10 | 4 | 4 | 135 |
| 3 | 10 | 10 | 4 | 4 | 90 |
| 4 | 10 | 10 | 4 | 4 | 45 |
| 5 | 10 | 10 | 4 | 4 | 0 |
| 6 | 10 | 10 | 4 | 4 | −45 |
| 7 | 10 | 10 | 4 | 4 | −90 |
| 8 | 10 | 10 | 4 | 4 | −135 |

MLC Leaf Positions for radiation source test

| Leaf number | Top bank- Leaf position (cm) | Bottom bank- Leaf position (cm) |
|---|---|---|
| 1 to 34 | −11 | 11 |
| 35 to 36 | 4 | 4 |
| 47 to 80 | −11 | 11 |

At operation 603, the image processing logic 120 detects field edges using a gradient process for each image. For example, the field center is determined in each image by detecting the field edges in each direction of the open field.

At operation 604, the image processing logic 120 computes an average of the field edges to determine the location of the radiation beam axis and determine a mean field center. The mean field center of each image is used to minimize the effect of field asymmetry.

At operation 605, the image processing logic 120 detects position of a ball bearing in the phantom in each of the 8 images. Specifically, the center of the ball bearing is determined using a normalized cross-correlation routine based on a reference image that is previously captured.

At operation 606, the image processing logic 120 for each gantry angle in the images, computes a distance between the mean field center and the position of the ball bearing.

At operation 607, the image processing logic 120 applies the computed distances and the gantry angle to a function that fits the data points along a plot that represents a projection of the distance between the radiation isocentre and the location of the ball bearing. The function represents the projection of the distance between the radiation isocentre and the location of the ball bearing for an MV source describing a circular orbit around the gantry axis of rotation.

At operation 608, the image processing logic 120 determines whether the MRI-Linac device is operating within a valid range based on the plot. Specifically, the image processing logic 120 determines whether the computed distances in the images between the mean field center and the position of the ball bearing exceeds an allowable threshold. In such cases, the image processing logic 120 may indicate that the MRI-Linac device is not operating within the valid range. The image processing logic 120 may compare the generated plot to an expected plot to determine whether a difference between the plots exceeds an allowable threshold to determine whether or not the device is operating within the valid range. In some cases, the image processing logic 120 may compare the location of the mean field center with the reference pixel to determine whether a difference exceeds an allowable threshold. In such cases when the threshold is exceeded, the image processing logic 120 determines that the device is not operating within the valid range.

Figure 6:
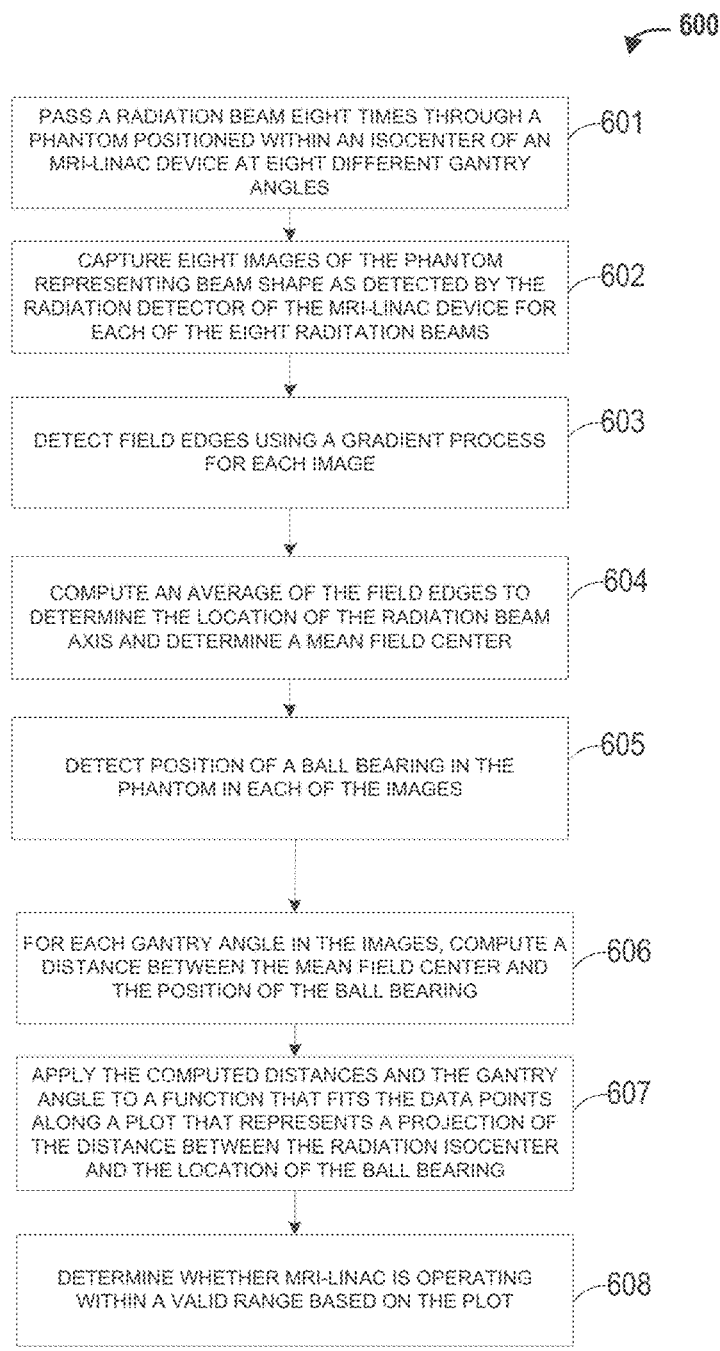
FIGS. 6-9 provide illustrative processes for testing an MRI-Linac device according to some examples of the disclosure.
Figure 7:
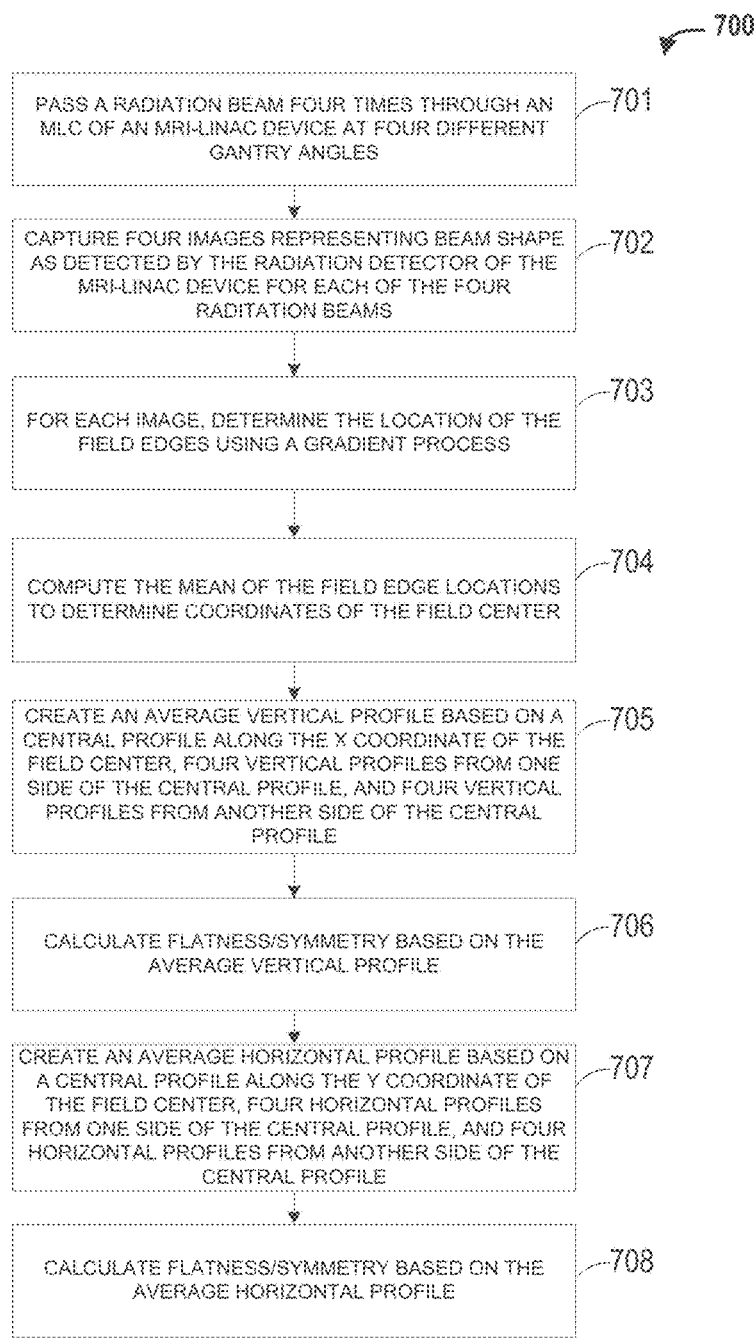
Figure 8:
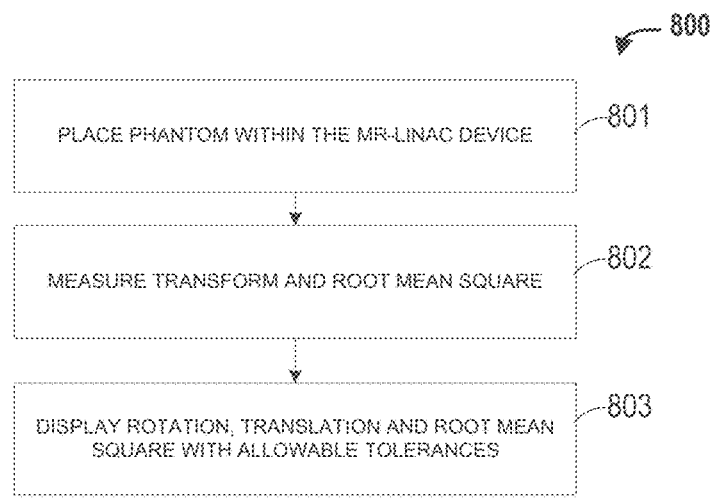
Figure 9:
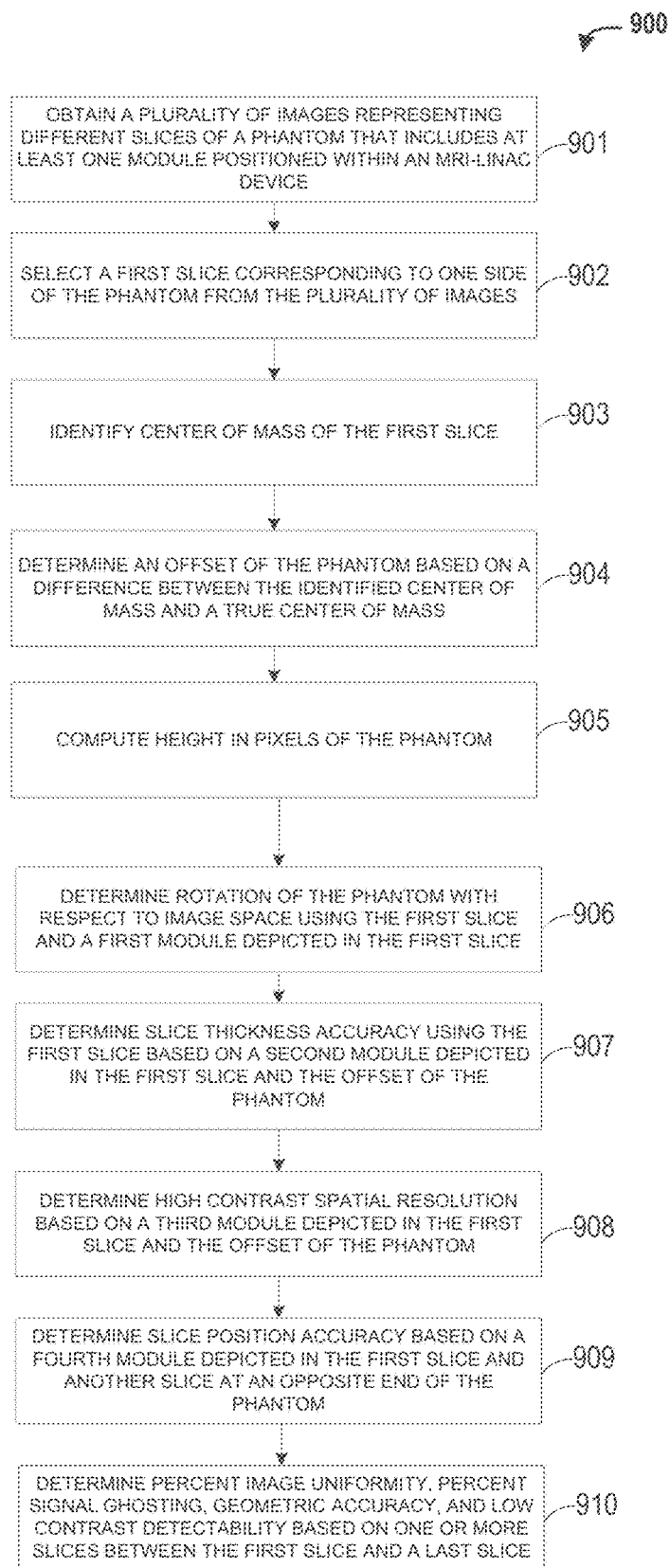

In some embodiments, the image processing logic 120, as a result of performing the operations of FIG. 6, generates a plurality of plots including a BB center coordinates versus gantry angle plot; field center coordinates versus gantry angle plot; radiation axis coordinates versus gantry angle plot; mean radiation axis coordinates versus time; and maximum displacement of axis from mean radiation isocentre over time plot.

In some embodiments, a user may select a validation procedure to perform that tests the output flatness symmetry versus the gantry angle. This validation procedure uses 4 open field images captured at 8 different gantry angles using an 8×20 cm field. This test calculates and reports output, flatness and symmetry of the four images. The 4 images are acquired at gantry angles of 180 degrees, 90 degrees, 0 degrees, and −270 degrees. Any other suitable additional or different angles may be used similarly.

The objective of this validation procedure is to determine flatness and symmetry in both radial and transverse directions. A relative measure of output is calculated from the central portion of each field. In an embodiment, the web-tool shown in FIG. 11 outputs this information. The test also outputs the relative output in the central 2×2 cm area of the panel. The web-tool presents plot views including flatness (radial & transverse) over time; symmetry (radial & transverse) overtime, output versus gantry angle; and average output over time.

In an embodiment, to start this validation procedure, an operator, via the web-tools shown in FIG. 11, inputs parameters that define the MRI-Linac device being tested and optionally inputs testing parameters. After the user inputs an instruction to begin the validation procedure, the processing circuitry 112 performs the process described in connection with FIG. 7 to verify flatness symmetry. In an embodiment, the user can specify the region of interest (e.g., a percentage of the open field) on which to perform the test.

At operation 701, the image processing logic 120 passes a radiation beam four times through an MLC of an MRI-Linac device at four different gantry angles. As shown in Table 9 below, the configuration of the jaws and the MLC leaf positions for each of the four radiation beams is defined:

TABLE 9

Jaw positions and gantry angle for the flatness symmetry versus gantry angle validation procedure

| Beam | Field size (cm) | | | | Gantry angle |
|---|---|---|---|---|---|
| number | X1 | X2 | Y1 | Y2 | Deg |
| 1 | 10 | 10 | 4 | 4 | 180 |
| 2 | 10 | 10 | 4 | 4 | 90 |
| 3 | 10 | 10 | 4 | 4 | 0 |
| 4 | 10 | 10 | 4 | 4 | 270 |

At operation 702, the image processing logic 120 captures four images representing beam shape as detected by the radiation detector of the MRI-Linac device for each of the four radiation beams.

At operation 703, the image processing logic 120 for each image, determines the location of the field edges using a gradient process.

At operation 704, the image processing logic 120 computes the mean of the field edge locations to determine coordinates of the field center. For example, an active contour algorithm iteratively modifies the points of an initial contour to minimize the internal energy of the contour (represented by the continuity and the curvature of the contour) and the image force (represented by the image gradient). During the iterative process, the algorithm moves the contour points toward the strongest gradient while minimizing the contour's curvature and maintaining regular spacing between the points. In the final solution, the points for which the second derivative of the contour exceeds a set threshold are identified as the field corners. Once the field corners are located, the remaining contour points can be grouped by field edge. The point on a given field edge is used to parameterize the field edge using a linear equation. This is repeated for the four field borders. The field center is calculated as a middle point of the four field borders found with the active contour algorithm. Additional information of field edge rotation may also be provided.

At operation 705, the image processing logic 120 creates an average vertical profile based on a central profile along the x coordinate of the field center, four vertical profiles from one side of the central profile and four vertical profiles from another side of the central profile. For example, the image processing logic 120 creates an average profile from 9 vertical profiles that include the central vertical profile containing the x coordinate and four vertical profiles on either side of the central profile.

At operation 706, the image processing logic 120 calculates flatness/symmetry based on the average vertical profile. Specifically, the flatness/symmetry indicates how similar the intensity of radiation is between and across different the region of interest. In an embodiment, 80% of the maximum open field intensity is determined centered on the field center. The image processing logic 120 computes or determines variation of intensity values from the center line and determines a level of equality between adjacent lines from the center line.

At operation 707, the image processing logic 120 creates an average horizontal profile based on a central profile along the y coordinate of the field center, four horizontal profiles from one side of the central profile and four horizontal profiles from another side of the central profile.

At operation 708, the image processing logic 120 calculates flatness/symmetry based on the average horizontal profile. Specifically, the flatness/symmetry indicates how similar the intensity of radiation is between and across different the region of interest. In an embodiment, 80% of the maximum open field intensity is determined centered on the field center. The image processing logic 120 computes or determines variation of intensity values from the center line and determines a level of equality between adjacent lines from the center line. In an embodiment, the image processing logic 120 generates an output indicating whether this test passes or fails if the variation in intensity between adjacent profiles and/or across a specified region is greater than an allowable threshold.

After the average horizontal and vertical profile flatness/symmetry is calculated, a 2×2 cm square area is segmented centered on the field center coordinates. An average of the intensity is obtained from inside of the square area. Specifically, flatness and symmetry are calculated in the transverse (x) and radial (y) directions based on the flattening filter (FF) beam and the flattening filter free (FFF) beam. For the FF beams, flatness is calculated as a percentage of the radio of maximum to minimum intensity points in the region of interest. The symmetry is calculated as a percentage of the ratio of mirror points from the center. The output is calculated in s a segment of 2×2 $cm^2$ square area centered on the field center coordinates. An average of the intensity reading inside the square area is taken and normalized to given the output. A conversion factor can be input by the user as a parameter to normalize the output depending on how the device normalization factor is defined. In an embodiment, an indication of whether the device passes or fails is provided to the user or a warning may be generated.

In some embodiments, a user may select a validation procedure to perform that tests the MR to MV alignment. This allows the MR to MV transform to be verified, such as on a regular basis. The results of this test are provided to the user in the web-tool, such as that shown in FIG. 11, and include the transform and the root mean square of the match between the MR and MV systems after the transform is applied. In an embodiment, a phantom is used for this test.

In an embodiment, to start this validation procedure, an operator, via the web-tools shown in FIG. 11, inputs parameters that define the MRI-Linac device being tested and optionally inputs testing parameters. After the user inputs an instruction to begin the validation procedure, the processing circuitry 112 performs the process described in connection with FIG. 8 to verify the MR to MV alignment.

Specifically, at operation 801, a phantom is placed within the MRI-Linac device. For example, an operator may select a phantom and position the phantom properly within the MRI-Linac device.

At operation 802, the image processing logic 120 measures transform and root mean square.

At operation 803, the image processing logic 120 displays rotation, translation and root mean square with allowable tolerances.

In some embodiments, a user may select a quality assessment procedure to perform that tests the MRI image quality of the MRI of the MRI-Linac device. The results of this test are provided to the user in the web-tool, such as that shown in FIG. 11, and include the verification of scan parameters, position and dimension information of a phantom, rotation of the phantom with respect to the image space, slice thickness accuracy, high contrast spatial resolution information, slice position accuracy, percent image uniformity (PIU), percent signal ghosting (PSG), low contrast detectability (LCD), and geometric accuracy information of the MRI device of the MRI-Linac device.

In an embodiment, to start one or more quality assessment procedures, an operator, via the web-tools shown in FIG. 11, inputs parameters that define the MRI-Linac device being tested and optionally inputs testing parameters. After the user inputs an instruction to begin the quality assessment procedure, the processing circuitry 112 performs the process described in connection with FIG. 9 to verify whether the MRI-Linac satisfies one or more quality metrics.

At operation 901, the image processing logic 120 obtains a plurality of images representing different slices of a phantom that includes at least one module positioned within an MRI-Linac device. For example, the processing circuitry 112 may instruct the MRI-Linac device to capture one or more MRI images of a phantom positioned within the MRI-Linac device. The phantom may include a plurality of modules (physical elements) each designed to provide a different quality assessment measure. The modules may be detected within different slices of the one or more MRI images that are captured. In some embodiments, a total of 11 slices may be obtained from the one or more images of the phantom.

In some embodiments, a test is performed to find the position of the phantom with respect to the axial field of view and also to verify the dimensions of the phantom. In some implementations, the output of this test is used to perform one or more additional quality assessment procedures. Specifically, the test is performed to find the distances in x and y directions between the center of the phantom slices and the center of the image and to find the height and width of the phantom image in millimetres. Operations 902-904 are performed to find the position of the phantom with respect to the axial field of view and to verify the dimensions of the phantom. The output of operations 902-904 are the coordinates of the central pixel of the first and last slices of the phantom, coordinates of the central pixel in the image depicting the phantom, a quantification of misalignment of the phantom in the images in the x and y coordinates, and a quantification of the height and width of the phantom in the first slice (and optionally additional slices).

In particular, at operation 902, the image processing logic 120 selects a first slice corresponding to one side of the phantom from the plurality of images. FIG. 10A shows the first slice 1010 that is selected at operation 902. The processing circuitry 112 applies the Otsu method to compute a threshold for the selected first slice 1010. The processing circuitry 112 converts the grayscale image of the first slice 1010 into a binary image using the computed threshold such that only the phantom has a pixel value of unity value. Specifically, the processing circuitry 112 processes the grayscale image of the first slice 1010 in a way that any pixel value that appears that exceeds a certain threshold is set to a first value (e.g., 0) and any other pixel is set to a second value (e.g., 1). In this way, the processing circuitry 112 can perform measurements and computations only on portions of the image slice that depict the phantom.

After converting the image of the first slice 1010 to a binary image, the processing circuitry 112 identifies the column number of the first and last pixels of the phantom. Specifically, the processing circuitry 112 identifies the first the column of pixels in the first slice 1010 that include a non-zero binary value. The processing circuitry 112 also identifies the last column of pixels in the first slice 1010 that include the non-zero binary value. Then the processing circuitry 112 identifies within each column between and including the first and last column, the set of rows that include non-zero binary values. The output of this step results in an outline of the phantom. In some embodiments, the first and last 5 rows of pixels are skipped in this identification process, as there may be some noise or white spots along the top and bottom edges of the image. The output of this process is a set of coordinates in terms of rows ($Ph_{rows}$) and columns ($Ph_{cols}$) that have binary non-zero values representing the phantom.

After identifying the outline of the phantom in the binary image, the processing circuitry 112 retrieves the grayscale image of the first slice 1010 and maps the outline of the phantom from the binary image to the grayscale image. The processing circuitry 112 creates a region of interest (ROI) around the phantom in the grayscale image based on the set of coordinates in terms of rows ($Ph_{rows}$) and columns ($Ph_{cols}$) that have binary non-zero values representing the phantom.

At operation 903, the image processing logic 120 identifies a center of mass of the first slice depicted in the first slice. For example, the processing circuitry 112 calculates the y coordinate of the phantom center ($Y_{ph}$) as the mean of the row values (row value positions) found for the ROI coordinates of the grayscale image of the first slice 1010 (e.g., the mean of the row values of only the portion of the image that depicts the phantom that includes the ROI of the phantom). The processing circuitry 112 calculates the x coordinate of the phantom center ($X_{ph}$) as the mean of the column values (column value positions) found for the ROI coordinates of the grayscale image of the first slice 1010 (e.g., the mean of the column values of only the portion of the image that depicts the phantom that includes the ROI of the phantom). In some embodiments, the image processing logic 120 repeats operations 901-903 (e.g., the calculation of the x and y coordinates of the phantom center) for a plurality of the image slices (e.g., image slices 5 and 7-11) in addition to the first image slice.

At operation 904, the image processing logic 120 determines an offset of the phantom based on a difference between the identified center of mass and a true center of mass. For example, the processing circuitry 112 computes the midpoint of the image space (e.g., the midpoint of the entire image that includes the first slice 1010). In an embodiment, to compute the midpoint of the entire image space, the processing circuitry 112 divides the header values for the columns and rows by 2 which output the x and y coordinates ($X_{sp}$, $Y_{sp}$), respectively. Specifically, the processing circuitry 112 finds the maximum column number and divides the number by 2 and finds the maximum row value and divides the row value by 2 to output the x and y coordinates. Next, the processing circuitry 112 computes the absolute difference between the phantom center and the image space center in the x and y directions in pixels to determine an offset of the phantom midpoint relative to the image space midpoint. The result of this computation is provided as $X_{ph\ diff\ pix}=|X_{sp}-X_{ph}|$ and $Y_{ph\ diff\ pix}=|Y_{sp}-Y_{ph}|$.

In some implementations, the processing circuitry 112 converts these differences to millimeters using a pixelspacing (P0) value that is precomputed and provided with the image header information. In some embodiments, the P0(1) represents height of the pixels and P0(2) represents the width of the pixels. In such cases, the value of the offset in millimeters is computed as $X_{ph\ diff\ mm}=X_{ph\ diff\ pix}*P0(2)$ and $Y_{ph\ diff\ mm}=Y_{ph\ diff\ pix}*P0(1)$.

At operation 905, the image processing logic 120 computes height in pixels of the phantom. For example, the processing circuitry 112 computes the height of the phantom in pixels as the difference between the maximum and minimum values of the $Ph_{rows}$ values. Similarly, the processing circuitry 112 computes the width of the phantom in pixels as the difference between the maximum and minimum values of the $Ph_{cols}$ values. The processing circuitry 112 then converts the width and height in pixels of the phantom to millimetres according to the expressions: (width of the phantom in pixels)*P0(2); (height of the phantom in pixels) *P0(1).

The image processing logic 120 retrieves (e.g., from user supplied information from the web-tool shown in FIG. 11) the real physical values of the phantom being used. Specifically, the image processing logic 120 obtains the actual physical height and width (e.g., 190 mm) of the phantom that is placed within the MRI-Linac device. The image processing logic 120 compares the computed height and width (dimensions) of the phantom derived from the images with the actual height and width of the phantom input by the user (or read from an RF ID code in the phantom). The image processing logic 120 determines whether a difference between the computed dimensions of the phantom and the actual dimensions of the phantom exceed an allowable threshold. In some cases, the user inputs the allowable threshold in the web-tool shown in FIG. 11. In response to determining that the difference exceeds the allowable threshold, the image processing logic 120 alerts the operator or user in the web-tool shown in FIG. 11; otherwise, the image processing logic 120 informs the operator that the MRI-Linac passed this image quality assessment procedure.

In some embodiments, the image processing logic 120 repeats the steps of computing the dimensions of the phantom and comparing the computed dimensions to the actual dimensions of the phantom for one or more additional slices (e.g., for slice 5 of the one or more images captured of the phantom). In some cases, the user selects for which slices that comparison between computed dimensions and actual dimensions is performed. In some cases, the user can set priorities to the slices such that if one slice is determined to have computed dimensions that exceed the actual dimensions by more than a threshold, the user is alerted about the difference exceeding the threshold if the slice is associated with a high priority. If the slice for which the computed dimensions that exceeds the actual dimensions by more than a threshold is associated with a low priority, the user is not alerted about the difference exceeding the threshold. In some cases, dimensions of the phantom are computed or derived from more than one image slice and are average. The average of the computations of the dimensions may be compared to the actual dimensions of the phantom. If the difference between the average computations of the dimensions and the actual dimensions of the phantom exceeds the allowable threshold, the user is alerted about the difference exceeding the threshold.

At operation 906, the image processing logic 120 determines rotation of the phantom with respect to image space using the first slice and a first module depicted in the first slice. Specifically, the image processing logic 120 determines the degrees of the phantom to help align the ROIs (the region of the image slices that depicts the phantom) for subsequent tests. The image processing logic 120 finds the rotation of the phantom based on the rotation of the edge of a first physical module 1016 present in the phantom image slice 1010 (e.g., a large central rectangle). For example, as shown in FIG. 10A, when the first physical module 1016 is a rectangle, the image processing logic 120 creates a rectangular ROI 1018 that is 120 mm wide and 20 mm high and places the rectangular ROI 1018 at a position within the first slice 1010 that is 3 mm higher or up in the y-direction from the phantom center of the first slice 1010. Namely, the rectangular ROI 1018 is positioned relative to the phantom center computed at operation 903. This results in a ROI 1018 being created around the center of the top and bottom long edges of the large central rectangle. The rectangle ROI 1018 that is created is placed parallel to the edges of the image space of the first slice 1010. The first physical module 1016 may be any other shape and in such cases, the image processing logic 120 creates a shape that resembles the shape of the first physical module 1016 as the ROI that is positioned over the first physical module 1016 depicted in the first slice 1010.

Next, the image processing logic 120 creates a matrix of the values of the segmented phantom image within the ROI 1018 that includes the rectangle that is created. Namely, the image processing logic 120 retrieves the pixel values of the pixels in the first slice 1010 that fall within the rectangle ROI 1018 that is placed on top of the first slice 1010 at the specified position. The image processing logic 120 identifies the matrix row numbers ($L_1$, $L_2$) of where the values change from 1 to 0 in the first column of the matrix and the last column of the matrix. Specifically, the first pixel of the large rectangle in the column at the left and right edge of the ROI 1018 that includes the first physical module 1016. The image processing logic 120 identifies the last pixel of the rectangle in the first and last column of the matrix ($M_1$, $M_2$). The result outputs P1 ($X_1$, $L_1$), P2 ($X_n$, $L_2$), P3 ($X_1$, $M_1$), and P4 ($X_n$, $M_2$), where n is the number of columns in the ROI matrix. P1, P2, P3, and P4 represent the points at which the first physical module 1016 intersect the rectangle ROI 1018 that is placed on top of the first physical module 1016 in the first slice 1010.

The image processing logic 120 computes the rotation of the phantom based on a slope of the top and bottom lines of the rectangle with respect to the axial field of view ($m_{top}$ and $m_{bottom}$, respectively). The slope represents the rotation of the rectangle with respect to the axial field of view (alpha), where alpha is calculated in degrees. Specifically, the image processing logic 120 computes the slope of top and bottom edges (e.g., long edges of the rectangle) of the first physical module 1016 relative to the corresponding top and bottom edges of the rectangle ROI that is placed on top of the first physical module 1016 in the first slice 1010. The slope and alpha is computed in accordance with the following expression: $m_{top} = (L_2-L_1)/(n-1)$, $m_{bottom} = (M_2-M_1)/(n-1)$, $m_{average} = (m_{top}+m_{bottom})/2$, alpha=$\tan^{-1}$ (average).

At operation 907, the image processing logic 120 determines slice thickness accuracy using the first slice based on a second module depicted in the first slice and the offset of the phantom. For example, the image processing logic 120 determines the slice thickness of the first slice 1010 from wire ramps that are included in the center of the phantom. In an embodiment, the slice thickness is determined to pass the quality assessment procedure when the slice thickness is approximately 0.7 mm.

In some embodiments, to compute the slice thickness, the image processing logic 120 creates two ROIs to be placed respectively around an upper wire ramp and a lower wire ramp based on predetermined values. The image processing logic retrieves previously computed phantom center locations and the rotation of the phantom to determine the slice thickness using the upper and lower wire ramps. In some implementations, the set values are used to set and place the two ROIs such that the vertices relative to the image file of the first slice 1010 are upper left: x=−48.83, y=−10.0; upper right: x=48.83, y=−10.0; lower right: x=−48.83, y=10.0; and lower right: x=48.83, y=10.0, or specified as follows:

tt1x=−48.83/P0(2); tt1y=−4.883/P0(1)
tt2x=48.83/P0(2); tt2y=−4.883/P0(1)
tt3x=48.83/P0(2); tt3y=−0.9766/P0(1)
tt4x=−48.83/P0(2); tt4y=−0.9766/P0(1)
tt5x=−48.83/P0(2); tt5y=2.9298/P0(1)
tt6x=48.83/P0(2); tt6y=2.9298/P0(1)
tt7x=48.83/P0(2); tt7y=−0.9766/P0(1)
tt8x=−48.83/P0(2); tt8y=−0.9766/P0(1)

The image processing logic 120 corrects the set values based on the position of the center of mass of the phantom computed in operation 903 by converting the set values from millimeter values to pixel values and applying the previously computed rotation. The corrected set values are referred to as $ROI_{full}$. Next, the image processing logic 120 retrieves all of the horizontal line profiles found in the $ROI_{full}$ and identifies the first and last row that consists entirely of pixel values that are less than a calculated threshold of the slice. In an embodiment, this calculated threshold is the same as that used in operation 902. If no qualifying rows are found (e.g., if the image processing logic 120 fails to identify a row that consists entirely of pixel values less than the calculated threshold), the test fails. Otherwise, the image processing logic 120 sets a trim $ROI_{full}$ value to be between the two rows of pixels ($ROI_{trimmed}$).

Next, the image processing logic 120 divides the rows of ROI$_{trimmed}$ vertically into two equal height ROIs (ROI$_{upper}$ and ROI$_{lower}$). The image processing logic 120 computes an average pixel value in each row of the ROI$_{upper}$ and ROI$_{lower}$. The image processing logic 120 selects the row of ROI$_{upper}$ with the highest average pixel value (Row$_{max-upper}$). The image processing logic 120 identifies the highest pixel value in Row$_{max-upper}$ and divides it by 2 P$_{half-max-upper}$. Next, the image processing logic 120 identifies the location of the first and last pixel value in Row$_{max-upper}$ that is higher than P$_{half-max-upper}$. The difference between the first and last locations provides the upper profile width in pixels. This value is converted to millimeter by multiplying by P0(2) and is output and stored as ProfileWidth$_{upper}$. The image processing logic 120 repeats the process of finding the ProfileWidth$_{lower}$ based on ROI$_{lower}$. Specifically, the image processing logic 120 selects the row of ROI$_{lower}$ with the highest average pixel value (Row$_{max-lower}$). The image processing logic 120 identifies the highest pixel value in Row$_{max-lower}$ and divides it by 2 P$_{half-max-lower}$. Next, the image processing logic 120 identifies the location of the first and last pixel value in Row$_{max-lower}$ that is higher than P$_{half-max-lower}$. The difference between the first and last locations provides the lower profile width in pixels. This value is converted to millimeter by multiplying by P0(2) and is output and stored as ProfileWidth$_{lower}$. In some embodiments, the image processing logic 120 outputs an image for presentation to a user via the web-tool shown in FIG. 11 that shows the location of the ROI$_{upper}$ and ROI$_{lower}$. The image processing logic 120 may also present two graphs (one for the upper and one for the lower wire) showing pixel locations versus value on Row$_{max-upper}$ and Row$_{max-lower}$, as well as P$_{half-max-upper}$ and P$_{half-max-lower}$.

The image processing logic 120 computes the measured slice thickness as: MeasuredSliceThickness=0.2* ((ProfileWidth$_{upper}$*ProfileWidth$_{lower}$)/ (ProfileWidth$_{upper}$*ProfileWidth$_{lower}$). The image processing logic 120 determines the slice thickness of the phantom being used TagSliceThickness (e.g., based on user input received from a user interface or web-tool shown in FIG. 11 or by retrieving the information from a header in the file that stores the one or more images of the phantom). The image processing logic 120 computes the slice thickness accuracy as SliceThicknessAccuracy=absolute value of (MeasuredSliceThickness−TagSliceThickness). The image processing logic 120 determines whether the computed slice thickness accuracy is less than an allowable threshold (e.g., 0.7 mm). The allowable threshold may be specified by a user via the web-tool shown in FIG. 11 or may be hard coded into the image processing logic 120. In response to determining that the slice thickness accuracy is less than an allowable threshold, the image processing logic 120 indicates that the MRI-Linac device passes the image quality assessment procedure. In response to determining that the slice thickness accuracy is more than the allowable threshold, the image processing logic 120 alerts the user (e.g., via the web-tool shown in FIG. 11) that the MRI-Linac device failed this image quality assessment procedure.

At operation 908, the image processing logic 120 determines high contrast spatial resolution based on a third module depicted in the first slice and the offset of the phantom. For example, the image processing logic 120 determines the spatial resolution of the first slice 1010 from a physical resolution pattern ROI 1018 in the phantom. In an embodiment, the high contrast spatial resolution is determined to pass the quality assessment procedure when the resolution is 1.0 mm or less.

In an embodiment, to perform this quality assessment procedure, the image processing logic 120 divides a portion of the image that corresponds to the physical resolution pattern ROI 1018 into 6 ROI's. The left two ROI's represent a resolution of 1.1 mm, the center 2 ROI's represent a resolution of 1.0 mm, and the right 2 ROI's represent a resolution of 0.9 mm. Each grouping of 2 ROIs with the same target resolution is read as horizontal lines (upper-left) and vertical lines (lower-right). The image processing logic 120 determines the lowest resolution at which 4 distinct holes can be found.

Specifically, to compute the high contrast spatial resolution, the image processing logic 120 creates six ROI's. One of the ROI's is positioned around the upper left series of holes (e.g., the physical resolution pattern ROI 1018) and one around the lower right series of holes (e.g., the physical resolution pattern ROI 1018). The image processing logic 120 creates the ROI's for each of three resolution spacings of 1.1 mm, 1.0 mm, and 0.9 mm regions based on previously set values, the phantom center location that was previously computed, and the rotation of the phantom. The vertices of the physical resolution pattern ROI 1018 are (in mm): upper left: x=−63.5, y=12.0; upper right: x=61.5, y=12.0; lower left: x=−63.5, y=62.0; and lower right: x=61.5, y=62.0. These vertices are converted from millimeters to pixels and then a rotation is applied to create ROI$_{full}$. The image processing logic 120 computes a threshold within the ROI$_{full}$ using the Otsu method. Then, the image processing logic 120 identifies the point P$_{upper-right}$ within the ROI$_{full}$ that is physically closest to the upper-right of the ROI$_{full}$ and has a value that is less than the computed threshold. The location of the three pairs 1030 (FIG. 10A) of ROIs is identified relative to P$_{upper-right}$. The upper left of each ROI pair relative to P$_{upper-right}$ are (in mm): upper-left of ROI$_{pair-1}$: x=−80.14, y=8.4; upper left of ROI$_{pair-2}$: x=−55.64, y=8.4; and upper left of ROI$_{pair-2}$: x=−33.64, y=9.4. These values are converted to pixel coordinates by applying the rotation that was previously computed.

Next, for each ROI$_{pair}$, the image processing logic 120 removes any horizontal and vertical lines on the four edges of the ROI that are made entirely of pixels that have values less than the computed threshold. The ROIs containing the 6 individual groupings of holes relative to the position of each ROI$_{pair}$ is calculated. These 6 ROIs (ROI$_1$, ROI$_2$, etc.) are shown as small boxes 1032 and 1033 within each of the three pairs 1030 in FIG. 10A. The upper ROIs (boxes 1032) extend a given distance in height and width from the upper-left of the matches ROI$_{pair}$, while the lower ROI (boxes 1033) extend the same distance from the lower right. These distances are 9 mm for ROI$_{pair-1}$, 8.5 mm for ROI$_{pair-2}$ and 8 mm for ROI$_{pair-3}$. These values are converted to pixel values by using the previously computed values for conversion.

The image processing logic 120 reads a profile in ROI of each row and finds the 4 rows with the highest average pixel values (Line$_1$, Line$_2$, etc.). The image processing logic 120 removes any pixels with values that are less than the average pixel value from the start and end of Line$_1$. The image processing logic 120 calculates a threshold on the remaining pixels using the Otsu method and groups the pixels in Line$_1$ into "on" (if they have values greater than the threshold) and "off" (if they are less than or equal to the threshold). The image processing logic 120 counts the number of transitions from on to off and determines the number of recognizable holes in that line. The image processing logic 120 repeats this process from Lines$_{2-4}$. If the number of holes is greater than four in any of Lines$_{1-4}$, then the image processing logic 120 determines that the resolution value for ROI$_1$ is satisfied. The image processing logic 120 repeats the process of finding and counting holes for ROI$_{2-6}$ (processing columns instead of rows for ROI$_2$, ROI$_4$ and ROI$_6$).

Each ROI is associated with a size in mm: ROI$_1$ and ROI$_2$ with 1.1 mm, ROI$_3$ and ROI$_4$ with 1.0 mm, and ROI$_5$ and ROI$_6$ with 0.9 mm. The horizontal resolution of the phantom is the lowest resolution of these resolutions ROI$_{1, 3, 5}$ that successfully resulted in more than 4 holes in a given line. The vertical resolution of the phantom is the lowest resolution of these resolutions ROI$_{2, 4, 6}$ that successfully resulted in more than 4 holes in a given line. In some embodiments, the image processing logic 120 determines whether the vertical and horizontal resolution is greater than an allowable threshold (e.g., 1.0 mm). The allowable threshold may be specified by a user via the web-tool shown in FIG. 11 or may be hard coded into the image processing logic 120. In response to determining that the resolution is greater than an allowable threshold, the image processing logic 120 indicates that the MRI-Linac device passes the image quality assessment procedure. In response to determining that the resolution is less than the allowable threshold, the image processing logic 120 alerts the user (e.g., via the web-tool shown in FIG. 11) that the MRI-Linac device failed this image quality assessment procedure.

In general, the phantom includes a physical resolution pattern ROI 1018 that allows the image processing logic 120 to compute the horizontal and vertical resolution of the MRI-Linac device. The physical resolution pattern ROI 1018 includes a plurality of regions, each configured to enable measurement of a different level of resolution along a different dimension (horizontal and vertical). The image processing logic 120 identifies each of these different regions and determines whether a known pattern is recognizable in the image captured from that region. If the pattern or a portion of the pattern is recognizable from the image captured from that region, then the image processing logic 120 determines that the level of resolution of the MRI-Linac is at least as good as the corresponding resolution of the region. Otherwise, the image processing logic 120 determines that the level of resolution of the MRI-Linac fails to meet the level of resolution associated with that region. For example, if each region includes a collection of holes, the image processing logic 120 determines whether a threshold number of the collection of holes in region is visible in the image that includes that region. If the threshold number of holes is visible, then the image processing logic 120 determines that the level of resolution of the MRI-Linac is at least as high as the resolution associated with the particular region. Once a region is found where the threshold number of holes is not found or recognizable, the image processing logic 120 determines that the MRI-Linac fails to provide the level of resolution associated with that region.

At operation 909, the image processing logic 120 determines slice position accuracy based on a fourth module depicted in the first slice and another slice at an opposite end of the phantom. For example, the image processing logic 120 determines the slice position accuracy from an image of a physical bar 1014 in the first slice 1010 and an image of the physical bar 1022 an eleventh slice 1020 in the phantom. In an embodiment, the slice position accuracy is determined to pass the quality assessment procedure when the bar length is determined to be 5.0 mm or less.

In an embodiment, to perform this quality assessment procedure, the image processing logic 120 generates ROIs around the left portion (e.g., left half of the bar) and right portion (e.g., right half of the bar) of the bar at the top of the phantom image in the first and eleventh slices 1010 and 1020, respectively. In an embodiment, this is performed on the grayscale images of the slices. In some implementations, the ROIs in the left and right portions is positioned at the below coordinates and corrections based on the rotation and phantom center (previously computed) are applied:

```
Left bar ROI:
PALt1x=-4.883/PO(2); PALt1y=-71.289/PO(1);
PALt2x=-1.953/PO(2); PALt2y=-71.289/PO(1);
PALt3x=-4.883/PO(2); PALt3y=-51.758/PO(1);
PALt4x=-1.953/PO(2); PALt4y=-51.758/PO(1);
Right bar ROI:
PARt1x=0.9766/PO(2); PARt1y=-71.289/PO(1);
PARt2x=3.906/PO(2); PARt2y=-71.289/PO(1);
PARt3x=0.9766/PO(2); PARt3y=-51.758/PO(1);
PARt4x=3.906/PO(2); PARt4y=-51.758/PO(1);
Apply corrections for rotation and phantom centre coordinates:
PALt11x = ((PALt1x * (cosd(alpha))) - (PALt1y * (sind(alpha)))) + xPhCntr ;
PALt11y = ((PALt1x * (sind(alpha))) + (PALt1y * (cosd(alpha)))) + yPhCntr ;
PALt12x = ((PALt2x * (cosd(alpha))) - (PALt2y * (sind(alpha)))) + xPhCntr ;
PALt12y = ((PALt2x * (sind(alpha))) + (PALt2y * (cosd(alpha)))) + yPhCntr ;
PALt13x = ((PALt3x * (cosd(alpha))) - (PALt3y * (sind(alpha)))) + xPhCntr ;
PALt13y = ((PALt3x * (sind(alpha))) + (PALt3y * (cosd(alpha)))) + yPhCntr ;
PALt14x = ((PALt4x * (cosd(alpha))) - (PALt4y * (sind(alpha)))) + xPhCntr ;
PALt14y = ((PALt4x * (sind(alpha))) + (PALt4y * (cosd(alpha)))) + yPhCntr ;
PARt11x = ((PARt1x * (cosd(alpha))) - (PARt1y * (sind(alpha)))) + xPhCntr ;
PARt11y = ((PARt1x * (sind(alpha))) + (PARt1y * (cosd(alpha)))) + yPhCntr ;
PARt12x = ((PARt2x * (cosd(alpha))) - (PARt2y * (sind(alpha)))) + xPhCntr ;
PARt12x = ((PARt2x * (cosd(alpha))) - (PARt2y * (sind(alpha)))) + yPhCntr ;
PARt13y = ((PARt3x * (sind(alpha))) + (PARt3y * (cosd(alpha)))) + xPhCntr ;
PARt13y = ((PARt3x * (sind(alpha))) + (PARt3y * (cosd(alpha)))) + yPhCntr ;
PARt14y = ((PARt4x * (sind(alpha))) + (PARt4y * (cosd(alpha)))) + xPhCntr ;
PARt14x = ((PARt4x * (cosd(alpha))) - (PARt4y * (sind(alpha)))) + yPhCntr ;
```

The image processing logic 120 extracts the profiles parallel to the edges of each ROI and applies the Otsu method to find a single threshold for these values. The image processing logic 120 segments and extracts the regions from the images using the single threshold. Next, the image processing logic 120 searches from the top to the bottom of the ROIs for the boundaries of the bar (e.g., the row number in the extracted region where the values change from black to white). For example, the image processing logic 120 searches the ROIs around the bar 1022 for the region 1024 where the pixel values change from black to white. Namely, as shown in FIG. 10A, the left portion of the ROI is found to change from black to white in the region 1024 while the right portion of the ROI of the bar continues to remain black in that region 1024. The image processing logic 120 computes the average column boundary value for each ROI (e.g., the image processing logic 120 computes the height of the left portion of the ROI and the height of the right portion of the ROI). The image processing logic 120 computes the difference between the column values for the left and right ROI (e.g., the image processing logic 120 determines whether the left portion of the ROI is shorter or smaller than the right portion of the ROI). If the image processing logic 120 determines that the left portion is longer than the right portion of the ROI, then the image processing logic 120 assigns a minus sign to the length.

The image processing logic 120 converts the computed difference in column values (e.g., the difference in heights of the two adjacent ROIs that are created over the bars 1014 and 1022) for the first slice 1010 to millimeter values by multiplying the value by the previously computed constant P0(1). The image processing logic 120 compares the computed difference in height in millimeters to an allowable threshold (e.g., 5 mm). If the difference in height is less than the allowable threshold, the image processing logic 120 determines that the slice position accuracy of the MRI-Linac passes this image quality assessment. The allowable threshold may be specified by a user via the web-tool shown in FIG. 11 or may be hard coded into the image processing logic 120. The image processing logic 120 indicates that the MRI-Linac device passes the image quality assessment procedure. In response to determining that the difference in height is greater than the allowable threshold, the image processing logic 120 alerts the user (e.g., via the web-tool shown in FIG. 11) that the MRI-Linac device failed this image quality assessment procedure.

The image processing logic 120 repeats the process of comparing the left and right bar ROI heights for another slice (e.g., the eleventh slice). The image processing logic 120 converts the computed difference in column values (e.g., the difference in heights of the two adjacent ROIs that are created over the bars 1014 and 1022) of the eleventh slice 1020 to millimeter values by multiplying the value by the previously computed constant P0(1). The image processing logic 120 compares the computed difference in height in millimeters to an allowable threshold (e.g., 4 mm). The allowable threshold for difference in height the eleventh slice 1020 may be smaller or greater than the allowable threshold used for the first slice 1010. If the difference in height is less than the allowable threshold, the image processing logic 120 determines that the slice position accuracy of the MRI-Linac passes this image quality assessment. The allowable threshold may be specified by a user via the web-tool shown in FIG. 11 or may be hard coded into the image processing logic 120. The image processing logic 120 indicates that the MRI-Linac device passes the image quality assessment procedure. In response to determining that the difference in height is greater than the allowable threshold, the image processing logic 120 alerts the user (e.g., via the web-tool shown in FIG. 11) that the MRI-Linac device failed this image quality assessment procedure.

At operation 910, the image processing logic 120 determines percent image uniformity, percent signal ghosting, geometric accuracy, and low contrast detectability based on one or more slices between the first slice and a last slice.

To determine the percent image uniformity (PIU) of the MRI-Linac device, the image processing logic performs an image quality assessment procedure on slice 7 of the one or more images of the phantom. In an embodiment, the PIU is determined to pass the quality assessment procedure when the PIU is determined to be greater than or equal to 87.5% for MRI systems with field strengths less than 3 Tesla. In an embodiment, the PIU is determined to pass the quality assessment procedure when the PIU is determined to be greater than or equal to 82.0% for MRI systems with a field strength of 3 Tesla.

The image processing logic 120 retrieves the images of the seventh slice 1040 (FIG. 10B) of the phantom and identifies the location of the phantom with respect to the axial field of view and the x and y coordinates of the center of the phantom. In some implementations, the image processing logic 120 performs operations similar to operations 902-904 to determine the coordinates of the center of the phantom that appears in the seventh slice 1040. Next, the image processing logic 120 generates a 200 cm$^2$ (79.789/P0(1) pixel radius) circular ROI at a position that is 5 pixels below the center of the phantom in the grayscale image of the seventh slice 1040. This circular ROI is depicted as the outer large white circle shown in FIG. 10B. The image processing logic 120 identifies the location of the maximum and minimum pixels within this circular ROI 1042. The image processing logic generates two circular ROIs 1042 and 1044 (shown in FIG. 10B) that are 1 cm$^2$ (5.642/P0(1) pixel radius) and positions each ROI 1042 and 1044 centered on the corresponding maximum and minimum pixel values within the larger circular ROI.

The image processing logic 1040 ensures that the smaller 1 cm$^2$ circular ROIs 1042 and 1044 are both fully within the larger 200 cm$^2$ circular ROT. To do this, the image processing logic 120 checks the distance from the maximum and minimum points to the center of the larger circular ROI and verifies that the distance is less than a threshold value (e.g., less than 79.789/P0(1)-5.642/P0(1)). If the distance is less than the threshold, then the small circular ROI is within the large circular ROT. If not, then the image processing logic 120 centers the small ROI as a point along the same line from the center of the large ROI (at the same angle) but at a distance of the threshold value from the center of the large circular ROI.

The image processing logic 120 computes the mean values of the pixels within each of the small ROIs 1042 and 1044 (meanSlice7MaxROI and meanSlice7MinROI). The image processing logic 120 computes the PIU as follows: PIU=100*(1−((meansSlice7MaxROI−meanSlice7MinROI)/(meanSlice7MaxROI+meanSlice7MinROI))). Specifically, the image processing logic 120 computes the PIU as a function of the mean values of the pixels within each of the small ROIs 1042 and 1044. The image processing logic 120 retrieves the magnetic strength of the MRI-Linac device that was used to capture the one or more images of the phantom. In an embodiment, this value is input by a user (e.g., via the web-tool shown in FIG. 11) when launching this quality assessment procedure and stored for retrieval by the image processing logic 120. In some embodiments, the magnetic strength is encoded in a header of the one or more image files of the images of the phantom and retrieved by the image processing logic 120.

The image processing logic 120 compares the computed PIU to an allowable threshold (e.g., 87.5% for MRI with magnetic field strength less than 3 Tesla or 82.0% for MRI with magnetic field strength of 3 Tesla). If the PIU is greater than the allowable threshold, the image processing logic 120 determines that the PIU of the MRI-Linac passes this image quality assessment. The allowable threshold may be specified by a user via the web-tool shown in FIG. 11 or may be hard coded into the image processing logic 120. The image processing logic 120 indicates that the MRI-Linac device passes the image quality assessment procedure. In response to determining that the PIU is less than the allowable threshold, the image processing logic 120 alerts the user (e.g., via the web-tool shown in FIG. 11) that the MRI-Linac device failed this image quality assessment procedure.

In some embodiments, the image processing logic 120 generates a graphic showing the large circular ROI and the small circular ROIs for the maximum and minimum locations. The image processing logic 120 presents this graphic to a user via the web-tool shown in FIG. 11.

To determine the percent signal ghosting (PSG) of the MRI-Linac device, the image processing logic 120 performs an image quality assessment procedure on slice 7 of the one or more images of the phantom. In some cases, the image processing logic 120 uses the large circular ROI generated to compute the PIU to determine the PSG. In an embodiment, the PSG is determined to pass the quality assessment procedure when the PSG is determined to be less than or equal to 0.025.

To determine the PSG, the image processing logic 120 computes the mean value of the pixels inside of the large circular ROI that was generated to compute the PIU. The image processing logic 120 generates four elliptical ROIs as shown in image 1050 in FIG. 10B. The four elliptical ROIs are generated to have an area of 10 cm$^2$ and positioned at the top, bottom, left and right of the phantom in the image of the seventh slice 1040. The ellipses may have a length to width ratio of approximately 4:1. In an embodiment, the ellipses are along but not against the edges of the field of view and are not placed against the edges of the phantom or against the edges. The ellipses are centered between the edges of the phantom. In some cases, the image processing logic 120 reduces the width of the ellipses to achieve this result and the lengths are increased to maintain the specified area.

Next, the image processing logic 120 computes the distance between the edge of the phantom and the edge of the field of view at each of the four edges. For each top edge, the image processing logic 120 checks the minimum row value from the delineation of the segmented phantom image. For the bottom edge, the image processing logic 120 subtracts the maximum row value from the delineation of the phantom image from the total number of rows obtained from the header of the image of the seventh slice. The image processing logic 120, for the left edge, checks the minimum column value from the delineation of the phantom. For the right edge, the image processing logic 120 subtracts the maximum column value from the total number of columns in the image. The result of these checks outputs the number of pixels between the edge of the phantom and the edge of the field of view at each edge. The image processing logic 120 ensures that these values are less than a threshold (e.g., 17.842/P0(2)) plus 6 pixels (3 on each side) to ensure that the ROI does not touch the edge of the phantom or the edge of the field of view.

Once the image processing logic 120 determines the space available to place the elliptical ROIs, the radii of the major and minor axes of the ellipses is set. To set these radii, the image processing logic 120 determines if the distance is less than the threshold (e.g., 17.842/P0(2)) and if so, the minor (short) axis radius for the ellipse is set to w_pxl=8.921/P0(2) and the major (long) axis radius is set to l_pxl=35.681/P0(1). If the value for the distance is greater than the threshold plus 6 pixels, the minor axis radius is set to the distance plus 6 pixels divided by 2 and the major axis radius is set to 318.31/(P0(1)*P0(2)) divided by the short axis radius to maintain the area of the ROI.

Next, the image processing logic 120 computes the mean pixel value within each of the four elliptical ROIs (meanTopROI being the mean of the top ellipses, meanBtmROI being the mean of the bottom ellipses, meanLftROI being the mean of the left ellipses, and meanRgtROI being the mean of the right ellipses). The image processing logic 120 computes the ghosting ratio based on these mean values as: Ghosting Ratio=absolute value (((meanTopROI+meanBtmROI)−(meanLftROI+meanRgtROI))/(2*meanLgROI)).

The image processing logic 120 compares the computed Ghosting Ratio to an allowable threshold (e.g., 0.025). If the Ghosting Ratio is less than the allowable threshold, the image processing logic 120 determines that the Ghosting Ratio of the MRI-Linac passes this image quality assessment. The allowable threshold may be specified by a user via the web-tool shown in FIG. 11 or may be hard coded into the image processing logic 120. The image processing logic 120 indicates that the MRI-Linac device passes the image quality assessment procedure. In response to determining that the Ghosting Ratio is greater than the allowable threshold, the image processing logic 120 alerts the user (e.g., via the web-tool shown in FIG. 11) that the MRI-Linac device failed this image quality assessment procedure.

In some embodiments, the image processing logic 120 generates a graphic showing the large circular ROI and the four elliptical ROIs at the top, bottom, left and right of the phantom. The image processing logic 120 presents this graphic to a user via the web-tool shown in FIG. 11.

To determine the low contrast detectability (LCD) of the MRI-Linac device, the image processing logic performs an image quality assessment procedure on slices 9, 10 and 11 of the one or more images of the phantom. In an embodiment, the LCD is determined to pass the quality assessment procedure when the image processing logic 120 computes a total score of 9 spokes for MRI systems with field strengths less than 3 Tesla. In an embodiment, the LCD is determined to pass the quality assessment procedure when the image processing logic 120 computes a total score of 37 spokes for MRI systems with a field strength of 3 Tesla.

For slice 8, the image processing logic 120 obtains the threshold computed in operations 902-905. Specifically, the threshold computed for finding the position of the phantom with respect to the axial field of view and the dimensions of the phantom. Next, the image processing logic 120 searches from the image center in both the horizontal and vertical directions to find the x and y coordinates of where a pixel value is less than the threshold. This results in $P_{left}$, $P_{right}$, $P_{top}$, $P_{bottom}$. The image processing logic 120 finds the center point ($P_{center}$) by averaging the x values of the $P_{left}$ and $P_{right}$ and the y values of the $P_{top}$ and $P_{bottom}$. In an 85 mm diameter circular area around the $P_{center}$, the image processing logic 120 computes the mean and the standard deviation of the pixel values. The image processing logic 120 applies a window level of (mean) and window width of (mean*standard deviation*0.003) to generate an image of the slice for display to a user (e.g., via the web-tool shown in FIG. 11). For example, the image processing logic 120 outputs the images 1060 shown in FIG. 10B. The user reviews the image and counts and inputs the number of spokes that are observed. The image processing logic 120 repeats the process or generating the image of the slice for display to the user for each of slices 9 to 11. The image processing logic 120 stores the number of spokes input by the user as being visible on slices 8-11.

The image processing logic 120 compares the stored number of spokes to an allowable threshold (e.g., 9 spokes for MRI with magnetic field strength less than 3 Tesla or 37 spokes for MRI with magnetic field strength of 3 Tesla). If the number of spokes is greater than the allowable threshold, the image processing logic 120 determines that the LCD of the MRI-Linac passes this image quality assessment. The allowable threshold may be specified by a user via the web-tool shown in FIG. 11 or may be hard coded into the image processing logic 120. The image processing logic 120 indicates that the MRI-Linac device passes the image quality assessment procedure. In response to determining that the LCD is less than the allowable threshold, the image processing logic 120 alerts the user (e.g., via the web-tool shown in FIG. 11) that the MRI-Linac device failed this image quality assessment procedure.

To determine the geometric accuracy (spatial linearity) of the MRI-Linac device, the image processing logic 120 performs an image quality assessment procedure on slice 5 of the one or more images of the phantom. In some cases, the image processing logic 120 obtains the previously computed width and height of the first slice 1070 and the height and diagonal dimensions of the fifth slice 1072 to determine the geometric accuracy. In an embodiment, the geometric accuracy is determined to pass the quality assessment procedure when the width and height of the first slice 1070 and the height and diagonal dimensions of the fifth slice 1072 are within 2.0 mm of a baseline (190.0 mm).

The image processing logic 120, for the first slice 1070, scales the image by 16 using a Lanczos interpolation over 8×8 pixel neighborhood. This allows for sub-pixel accuracy on the various dimensions. The image processing logic 120 starts to scan horizontally from left to right and vertically from up to down to find the first pixel with a value that is less than the first slice 1070 threshold. The length of the lines from the leftmost pixel to the rightmost pixel and the top pixel to the bottom pixel are the scaled width and height of the phantom. The image processing logic 120 divides the values of the lengths of the lines by 160.0 to reverse the scaling. For the fifth slice 1072, the image processing logic 120 repeats the process of horizontally scanning from left to right and vertically from up to down to find the first pixel with a value that is less than the fifth slice 1072 threshold. The length of the lines from the leftmost pixel to the rightmost pixel and the top pixel to the bottom pixel are the scaled width and height of the phantom in the fifth slice 1072. The image processing logic 120 divides the values of the lengths of the lines computed for the fifth slice 1072 by 160.0 to reverse the scaling.

Next, the image processing logic 120 repeats the process of computing the lines for each diagonal (45 degrees) through the slice's COM. The image processing logic 120 converts all the lines to millimeters using previously computed values. The image processing logic 120 then determines whether the computed lengths satisfy allowable thresholds (which may be user provided). If the lengths are within 2.0 millimeters of the allowable threshold, the image processing logic 120 determines that the geometric accuracy of the MRI-Linac passes this image quality assessment. The image processing logic 120 indicates that the MRI-Linac device passes the image quality assessment procedure. In response to determining that the lengths are outside of the allowable threshold, the image processing logic 120 alerts the user (e.g., via the web-tool shown in FIG. 11) that the MRI-Linac device failed this image quality assessment procedure.

In some embodiments, the image processing logic 120 determines the geometric accuracy of the sagittal view slice if one is present. The length should be within 2.0 mm of the ideal length of 148.0 mm. The image processing logic 120 finds the sagittal view slice's threshold and divides it by 2. The image processing logic 120 creates a binary image of the pixels with values greater than the threshold. The image processing logic 120 scans each row in the binary image and fills any interior empty spaces that are 20 pixels or less wide. Based on the modified binary image, the image processing logic 120 calculates the COM of the slice. The image processing logic 120 reads columns of pixels from the binary image top to bottom at the COM x and 2 columns on either side (total of 5 columns) to find the top and bottom "on" pixels. The difference between the top and bottom is the length of that column in pixels. The image processing logic 120 sums the results and divides the total by 5 to provide the sagittal length in pixels. The image processing logic 120 converts this value to millimeters using previously determined factors or values. In an embodiment, the image processing logic 120 outputs an image representing this result.

FIG. 11 illustrates an example web-based interface 1100 for testing the MRI-Linac device according to some examples of the disclosure. In some embodiments, the user accesses the web-based interface 1100 via the Internet by accessing a website. The web-based interface 1100 an input MRI-Linac device parameters option 1110, an upload radiation detector images and/or MRI images option 1120, a specify thresholds and allowable tolerances option 1130, a select validation procedure option 1140, an instruct MRI-Linac device to being select option 1150, a select imaging quality assessment procedure option 1160, and a pass/fail report and image processing results display 1170.

In response to receiving a user selection of the input MRI-Linac device parameters option 1110, a prompt is provided to the user that allows the user to input any of the parameters discussed above that are used to generate images of the MRI-Linac device for testing. For example, the user can specify the parameters of the MLC and Jaw, such as the leaf size and width and can specify the magnetic field strength of the MRI-Linac device. The user can also specify various parameters (e.g., the number and types and locations of physical modules in one or more phantoms) of phantoms used to perform the imaging quality assessment and other validation procedures.

In some embodiments, the user can select the upload radiation detector images and/or MRI images by selecting option 1120. Specifically, any of the images discussed above for performing the validation procedures or quality assessment can be previously captured and stored and uploaded by the user. After the user uploads the images and/or after the images are captured, the user can specify the allowable thresholds of the MRI-Linac device that are used in determining whether the MRI-Linac device passes or fails a given validation procedure or quality assessment. To do so, the user selects option 1130. In response, a list of validation procedures and quality assessments are presented with the default thresholds of the tests. The user can modify any of the default values and the modified values are used by the image processing logic 120 to determine whether a given test passes or fails.

The user can select a validation procedure to perform by selecting option 1140. In response to receiving the user selection of option 1140, the web-based interface 1100 presents the user with a list of available validation procedures. For example, the web-based interface 1100 presents an interactive list including the position validation procedure of the MLC, a radiation source and imaging detector movement validation procedure, a linear accelerator and MRI imaging device alignment validation procedure, and a linear accelerator flatness symmetry validation procedure. The user can select any one or all of the listed procedures to perform on the uploaded images or on newly captured images of the MRI-Linac device.

The user can select an imaging quality assessment procedure (or imaging quality assessment) to perform by selecting option 1160. In response to receiving the user selection of option 1160, the web-based interface 1100 presents the user with a list of available imaging quality assessments. For example, the web-based interface 1100 presents an interactive list including the quality assessment procedure for checking a rotation of the phantom with respect to image space, computing slice thickness accuracy, computing high contrast spatial resolution, checking slice position accuracy, computing percent image uniformity, computing percent signal ghosting, computing low contrast detectability, or computing geometric accuracy. The user can select any one or all of the listed procedures to perform on the uploaded images or on newly captured images of the MRI-Linac device.

In some embodiments, when a given set of images are not previously captured and available for a user to upload, the user can select option 1150 to instruct the MRI-Linac device to perform a given operation to capture the set of images suitable for the procedure(s) selected by options 1140 and 1160. In some embodiments, the web-based interface 1100 instructs an operator on how to position a phantom and/or the MLC to capture the appropriate images for a given procedure. In some embodiments, the web-based interface 1100 communicates with the MRI-Linac device to automatically set the MLC of the MRI-Linac device to the appropriate configuration for capturing images for a given procedure.

After the images are captured or uploaded, the web-based interface 1100 presents the results of all of the procedures selected by the user with options 1140 and 1160 in the results display 1170. Results display 1170 may include any graphics that are generated by the image processing logic 120. The user can select any one of the displayed results to obtain further information about why a given procedure or test passed or failed.

ADDITIONAL NOTES

As previously discussed, respective electronic computing systems or devices may implement one or more of the methods or functional operations as discussed herein. In various embodiments, such electronic computing systems or devices operates as a standalone device or may be connected (e.g., networked) to other machines. For instance, such computing systems or devices may operate in the capacity of a server or a client machine in server-client network environment, or as a peer machine in a peer-to-peer (or distributed) network environment. Features of computing systems or devices may be embodied by a personal computer (PC), a tablet PC, a Personal Digital Assistant (PDA), a cellular telephone, a web appliance, or any machine capable of executing instructions (sequential or otherwise) that specify actions to be taken by that machine.

As also indicated above, the functionality discussed above may be implemented by instructions, logic, or other information storage on a machine-readable medium. While the machine-readable medium may have been described with various examples with reference to be a single medium, the term "machine-readable medium" may include a single medium or multiple media (e.g., a centralized or distributed database, and/or associated caches and servers) that store the one or more transitory or non-transitory instructions or data structures. The term "machine-readable medium" shall also be taken to include any tangible medium that is capable of storing, encoding or carrying transitory or non-transitory instructions for execution by the machine and that cause the machine to perform any one or more of the methodologies of the present disclosure, or that is capable of storing, encoding or carrying data structures utilized by or associated with such instructions.

The above detailed description includes references to the accompanying drawings, which form a part of the detailed description. The drawings show, by way of illustration but not by way of limitation, specific embodiments in which the disclosure can be practiced. These embodiments are also referred to herein as "examples." Such examples can include elements in addition to those shown or described. However, this disclosure also contemplates examples in which only those elements shown or described are provided. Moreover, the disclosure also contemplates examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a," "an," "the," and "said" are used when introducing elements of aspects of the disclosure or in the embodiments thereof, as is common in patent documents, to include one or more than one or more of the elements, independent of any other instances or usages of "at least one" or "one or more." In this document, the term "or" is used to refer to a nonexclusive or, such that "A or B" includes "A but not B," "B but not A," and "A and B," unless otherwise indicated.

In the appended claims, the terms "including" and "in which" are used as the plain-English equivalents of the respective terms "comprising" and "wherein." Also, in the following claims, the terms "comprising," "including," and "having" are intended to be open-ended to mean that there may be additional elements other than the listed elements, such that after such a term (e.g., comprising, including, having) in a claim are still deemed to fall within the scope of that claim. Moreover, in the following claims, the terms "first," "second," and "third," etc., are used merely as labels, and are not intended to impose numerical requirements on their objects.

The present disclosure also relates to a computing system adapted, configured, or operated for performing the operations herein. This system may be specially constructed for the required purposes, or it may comprise a general purpose computer selectively activated or reconfigured by a computer program (e.g., instructions, code, etc.) stored in the computer. The order of execution or performance of the operations in embodiments of the disclosure illustrated and described herein is not essential, unless otherwise specified. That is, the operations may be performed in any order, unless otherwise specified, and embodiments of the disclosure may include additional or fewer operations than those disclosed herein. For example, it is contemplated that executing or performing a particular operation before, contemporaneously with, or after another operation is within the scope of aspects of the disclosure.

In view of the above, it will be seen that the several objects of the disclosure are achieved and other advantageous results attained. Having described aspects of the disclosure in detail, it will be apparent that modifications and variations are possible without departing from the scope of aspects of the disclosure as defined in the appended claims. As various changes could be made in the above constructions, products, and methods without departing from the scope of aspects of the disclosure, it is intended that all matter contained in the above description and shown in the accompanying drawings shall be interpreted as illustrative and not in a limiting sense.

The examples described herein may be implemented in a variety of embodiments. For example, one embodiment includes a computing device including processing hardware (e.g., a processor or other processing circuitry) and memory hardware (e.g., a storage device or volatile memory) including instructions embodied thereon, such that the instructions, which when executed by the processing hardware, cause the computing device to implement, perform, or coordinate the electronic operations for these techniques and system configurations. Another embodiment discussed herein includes a computer program product, such as may be embodied by a machine-readable medium or other storage device, which provides the transitory or non-transitory instructions to implement, perform, or coordinate the electronic operations for these techniques and system configurations. Another embodiment discussed herein includes a method operable on processing hardware of the computing device, to implement, perform, or coordinate the electronic operations for these techniques and system configurations.

In further embodiments, the logic, commands, or transitory or non-transitory instructions that implement aspects of the electronic operations described above, may be provided in a distributed or centralized computing system, including any number of form factors for the computing system such as desktop or notebook personal computers, mobile devices such as tablets, netbooks, and smartphones, client terminals and server-hosted machine instances, and the like. Another embodiment discussed herein includes the incorporation of the techniques discussed herein into other forms, including into other forms of programmed logic, hardware configurations, or specialized components or modules, including an apparatus with respective means to perform the functions of such techniques. The respective algorithms used to implement the functions of such techniques may include a sequence of some or all of the electronic operations described above, or other aspects depicted in the accompanying drawings and detailed description below.

The above description is intended to be illustrative, and not restrictive. For example, the above-described examples (or one or more aspects thereof) may be used in combination with each other. In addition, many modifications may be made to adapt a particular situation or material to the teachings of the disclosure without departing from its scope. While the dimensions, types of materials and example parameters, functions, and implementations described herein are intended to define the parameters of the disclosure; they are by no means limiting and are exemplary embodiments. Many other embodiments will be apparent to those of skill in the art upon reviewing the above description. The scope of the disclosure should, therefore, be determined with reference to the appended claims, along with the full scope of equivalents to which such claims are entitled.

Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the disclosure should be determined with reference to the appended claims, along with the full scope of equivalents to which such claims are entitled.

What is claimed is:

1. A method for determining image quality of a radiotherapy apparatus comprising an integrated linear accelerator and magnetic resonance imaging (MRI) imaging device (MR-Linac), the method comprising:
    selecting a quality assessment procedure associated with the MRI imaging device of the MR-Linac;
    obtaining a plurality of images from the MRI imaging device of a phantom that includes at least one module;
    processing, based on the selected quality assessment procedure, a feature in the plurality of images representing components in the at least one module;
    computing an image quality attribute associated with the MRI imaging device based on the processed feature;
    determining whether the image quality attribute satisfies an allowable criterion; and
    determining whether the MR-Linac is validly operating in response to determining that the image quality attribute satisfies the allowable criterion.

2. The method of claim 1 further comprising adjusting one or more characteristics of the MR-Linac in response to determining that the image quality attribute fails to satisfy the allowable criterion.

3. The method of claim 1, wherein the quality assessment procedure is a first quality assessment procedure for computing a position of the phantom with respect to axial field of view and computing dimensions of the phantom.

4. The method of claim 3 further comprising:
    selecting a first image of the plurality of images;
    binarizing the first image such that the phantom shown in the first image has a unity pixel value;
    identifying a column number of first and last pixels of the phantom in each row of pixels;
    generating a region of interest (ROI) around the phantom based on the identified column numbers;
    identifying a center of mass of the ROI based on the identified column numbers;
    identifying a center of the first image;
    computing a difference between coordinates of the phantom and the center of the first image to determine misalignment of the phantom; and
    computing a height and width of the phantom based on the ROI.

5. The method of claim 1, wherein the quality assessment procedure is part of a plurality of quality assessment procedures that includes at least one of a quality assessment procedure for checking a rotation of the phantom with respect to image space, computing slice thickness accuracy, computing high contrast spatial resolution, checking slice position accuracy, computing percent image uniformity, computing percent signal ghosting, computing low contrast detectability, or computing geometric accuracy.

6. A method for performing quality assessment of a radiotherapy apparatus comprising an integrated linear accelerator and magnetic resonance imaging (MRI) imaging device (MR-Linac), the method comprising:
  selecting a validation procedure associated with the linear accelerator of the MR-Linac and a quality assessment procedure associated with the MRI imaging device of the MR-Linac;
  obtaining a first plurality of images from an imaging detector each associated with a given radiation beam of a plurality of radiation beams that passes through a multi-leaf collimator (MLC) that has been adjusted based on the selected validation procedure;
  obtaining a second plurality of images from the MRI imaging device of a phantom that includes at least one module;
  processing the first and second plurality of images based on the selected validation and quality assessment procedures; and
  determining whether the MR-Linac is operating within a valid range based on attributes of the first and second plurality of images determined from processing the first and second plurality of images.

7. The method of claim 6 further comprising adjusting one or more characteristics of the MR-Linac in response to determining that the MR-Linac is operating outside of the valid range.

8. The method of claim 7, wherein the one or more characteristics are determined based on the selected validation or quality assessment procedure.

9. A system comprising:
  one or more processors configured to perform operations comprising:
    selecting a quality assessment procedure associated with a magnetic resonance imaging (MRI) imaging device of a magnetic resonance linear accelerator (MR-Linac);
    obtaining a plurality of images from the MRI imaging device of a phantom that includes at least one module;
    processing, based on the selected quality assessment procedure, a feature in the plurality of images representing components in the at least one module;
    computing an image quality attribute associated with the MRI imaging device based on the processed feature;
    determining whether the image quality attribute satisfies an allowable criterion; and
    determining whether the MR-Linac is validly operating in response to determining that the image quality attribute satisfies the allowable criterion.

10. The system of claim 9, the operations further comprising adjusting one or more characteristics of the MR-Linac in response to determining that the image quality attribute fails to satisfy the allowable criterion.

11. The system of claim 9, wherein the quality assessment procedure is a first quality assessment procedure for computing a position of the phantom with respect to axial field of view and computing dimensions of the phantom.

12. The system of claim 11, the operations further comprising:
  selecting a first image of the plurality of images,
  binarizing the first image such that the phantom shown in the first image has a unity pixel value;
  identifying a column number of first and last pixels of the phantom in each row of pixels;
  generating a region of interest (ROI) around the phantom based on the identified column numbers;
  identifying a center of mass of the ROI based on the identified column numbers;
  identifying a center of the first image;
  computing a difference between coordinates of the phantom and the center of the first image to determine misalignment of the phantom; and
  computing a height and width of the phantom based on the ROI.

13. The system of claim 9, wherein the quality assessment procedure is part of a plurality of quality assessment procedures that includes at least one of a quality assessment procedure for checking a rotation of the phantom with respect to image space, computing slice thickness accuracy, computing high contrast spatial resolution, checking slice position accuracy, computing percent image uniformity, computing percent signal ghosting, computing low contrast detectability, or computing geometric accuracy.

14. A non-transitory computer readable medium comprising computer readable instructions that, when executed by one or more processors, configure the one or more processors to perform operations comprising:
  selecting a quality assessment procedure associated with a magnetic resonance imaging (MRI) imaging device of a magnetic resonance linear accelerator (MR-Linac);
  obtaining a plurality of images from the MRI imaging device of a phantom that includes at least one module;
  processing, based on the selected quality assessment procedure, a feature in the plurality of images representing components in the at least one module;
  computing an image quality attribute associated with the MRI imaging device based on the processed feature;
  determining whether the image quality attribute satisfies an allowable criterion; and
  determining whether the MR-Linac is validly operating in response to determining that the image quality attribute satisfies the allowable criterion.

15. The non-transitory computer readable medium of claim 14, the operations further comprising adjusting one or more characteristics of the MR-Linac in response to determining that the image quality attribute fails to satisfy the allowable criterion.

16. The non-transitory computer readable medium of claim 14, wherein the quality assessment procedure is a first quality assessment procedure for computing a position of the phantom with respect to axial field of view and computing dimensions of the phantom.

17. The non-transitory computer readable medium of claim 16, the operations further comprising:
  selecting a first image of the plurality of images;
  binarizing the first image such that the phantom shown in the first image has a unity pixel value;
  identifying a column number of first and last pixels of the phantom in each row of pixels;
  generating a region of interest (ROI) around the phantom based on the identified column numbers;
  identifying a center of mass of the ROI based on the identified column numbers;
  identifying a center of the first image;
  computing a difference between coordinates of the phantom and the center of the first image to determine misalignment of the phantom; and computing a height and width of the phantom based on the ROI.

18. A system comprising:
one or more processors configured to perform operations comprising:
- selecting a validation procedure associated with a linear accelerator of a magnetic resonance linear accelerator (MR-Linac) and a quality assessment procedure associated with a magnetic resonance imaging (MRI) imaging device of the MR-Linac;
- obtaining a first plurality of images from an imaging detector each associated with a given radiation beam of a plurality of radiation beams that passes through a multi-leaf collimator (MLC) that has been adjusted based on the selected validation procedure;
- obtaining a second plurality of images from the MRI imaging device of a phantom that includes at least one module;
- processing the first and second plurality of images based on the selected validation and quality assessment procedures; and
- determining whether the MR-Linac is operating within a valid range based on attributes of the first and second plurality of images determined from processing the first and second plurality of images.

19. The system of claim 18, the operations further comprising adjusting one or more characteristics of the MR-Linac in response to determining that the MR-Linac is operating outside of the valid range.

20. The system of claim 19, wherein the one or more characteristics are determined based on the selected validation or quality assessment procedure.

\* \* \* \* \*

UNITED STATES PATENT AND TRADEMARK OFFICE
CERTIFICATE OF CORRECTION

| | | |
|---|---|---|
| PATENT NO. | : 12,343,566 B2 | Page 1 of 1 |
| APPLICATION NO. | : 18/636853 | |
| DATED | : July 1, 2025 | |
| INVENTOR(S) | : Letourneau et al. | |

It is certified that error appears in the above-identified patent and that said Letters Patent is hereby corrected as shown below:

On the Title Page

On page 2, in Column 2, under item (56), "Other Publications", Line 9, delete "persuant" and insert --pursuant-- therefor In the Claims In Column 46, Line 3, in Claim 12, delete "images," and insert --images;-- therefor Signed and Sealed this
Thirtieth Day of September, 2025

John A. Squires
*Director of the United States Patent and Trademark Office*